US009789482B2

(12) United States Patent
Link et al.

(10) Patent No.: US 9,789,482 B2
(45) Date of Patent: Oct. 17, 2017

(54) METHODS OF INTRODUCING A FLUID INTO DROPLETS

(71) Applicant: President and Fellows of Harvard College, Cambridge, MA (US)

(72) Inventors: Darren Roy Link, Lexington, MA (US); David A. Weitz, Bolton, MA (US); Galder Cristobal-Azkarate, Bordeaux (FR); Zhengdong Cheng, College Station, TX (US); Keunho Ahn, San Diego, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/255,101

(22) Filed: Apr. 17, 2014

(65) Prior Publication Data

US 2014/0305799 A1      Oct. 16, 2014

Related U.S. Application Data

(63) Continuation of application No. 11/360,845, filed on Feb. 23, 2006, now Pat. No. 8,765,485, which is a
(Continued)

(51) Int. Cl.
*B01L 3/00* (2006.01)
*B01F 5/06* (2006.01)
(Continued)

(52) U.S. Cl.
CPC .......... *B01L 3/5027* (2013.01); *B01F 5/0646* (2013.01); *B01F 5/0655* (2013.01);
(Continued)

(58) Field of Classification Search
CPC ................ B01F 13/006; B01F 13/0071; B01F 13/0072; B01L 3/5027; B01L 3/50273;
(Continued)

(56) References Cited

U.S. PATENT DOCUMENTS 2,692,800 A   10/1954   Nichols et al.
3,816,331 A   6/1974    Brown et al.
(Continued)

FOREIGN PATENT DOCUMENTS

AU   200039611    10/2000
CA   2438955 A1    8/2002
(Continued)

OTHER PUBLICATIONS

European Office Action dated Apr. 29, 2014 for EP 08165420.4.
(Continued)

*Primary Examiner* — Brian R Gordon
(74) *Attorney, Agent, or Firm* — Wolf, Greenfield & Sacks, P.C.

(57) ABSTRACT

Various aspects of the present invention relate to the control and manipulation of fluidic species, for example, in microfluidic systems. In one aspect, the invention relates to systems and methods for making droplets of fluid surrounded by a liquid, using, for example, electric fields, mechanical alterations, the addition of an intervening fluid, etc. In another aspect, the invention relates to systems and methods for dividing a fluidic droplet into two droplets, for example, through charge and/or dipole interactions with an electric field. The invention also relates to systems and methods for fusing droplets, according to another aspect of the invention, for example, through charge and/or dipole interactions. Another aspect of the invention provides the ability to determine droplets, or a component thereof, for example, using fluorescence and/or other optical techniques (e.g., microscopy), or electric sensing techniques such as dielectric sensing.

11 Claims, 22 Drawing Sheets

Related U.S. Application Data continuation of application No. PCT/US2004/027912, filed on Aug. 27, 2004.

(60) Provisional application No. 60/498,091, filed on Aug. 27, 2003.

(51) Int. Cl.

| | | |
|---|---|---|
| *B01F 13/00* | (2006.01) | |
| *B01J 19/00* | (2006.01) | |
| *G01N 15/14* | (2006.01) | |
| *B01F 5/02* | (2006.01) | |

(52) U.S. Cl.
CPC .......... *B01F 5/0682* (2013.01); *B01F 5/0689* (2013.01); *B01F 13/0071* (2013.01); *B01F 13/0074* (2013.01); *B01F 13/0076* (2013.01); *B01J 19/0093* (2013.01); *B01L 3/502784* (2013.01); *G01N 15/14* (2013.01); *B01F 5/0256* (2013.01); *B01J 2219/00783* (2013.01); *B01J 2219/00862* (2013.01); *B01L 2200/0673* (2013.01); *B01L 2300/0864* (2013.01); *B01L 2300/0867* (2013.01); *B01L 2400/0415* (2013.01); *B01L 2400/0439* (2013.01); *B01L 2400/0487* (2013.01); *Y10S 436/807* (2013.01); *Y10T 436/118339* (2015.01); *Y10T 436/2525* (2015.01); *Y10T 436/2575* (2015.01)

(58) Field of Classification Search
CPC ........ B01L 3/502792; B01L 3/502784; B01L 2200/0673; B01L 2300/0864; B01L 2400/0655
USPC ................. 436/180; 204/450–452, 600–601; 422/502–504, 68.1
See application file for complete search history.

(56) References Cited

U.S. PATENT DOCUMENTS

| | | | |
|---|---|---|---|
| 3,982,541 | A | 9/1976 | L'Esperance, Jr. |
| 4,059,552 | A | 11/1977 | Zweigle et al. |
| 4,279,345 | A | 7/1981 | Allred |
| 4,508,265 | A | 4/1985 | Jido |
| 4,618,476 | A | 10/1986 | Columbus |
| 4,795,330 | A | 1/1989 | Noakes et al. |
| 4,829,996 | A | 5/1989 | Noakes et al. |
| 4,853,336 | A | 8/1989 | Saros et al. |
| 4,865,444 | A | 9/1989 | Green et al. |
| 4,931,225 | A | 6/1990 | Cheng |
| 4,996,004 | A | 2/1991 | Bucheler et al. |
| 5,149,625 | A | 9/1992 | Church et al. |
| 5,204,112 | A | 4/1993 | Hope et al. |
| 5,378,957 | A | 1/1995 | Kelly |
| 5,452,955 | A | 9/1995 | Lundstrom |
| 5,512,131 | A | 4/1996 | Kumar et al. |
| 5,617,997 | A | 4/1997 | Kobayashi et al. |
| 5,681,600 | A | 10/1997 | Antinone et al. |
| 5,762,775 | A | 6/1998 | DePaoli et al. |
| 5,851,769 | A | 12/1998 | Gray et al. |
| 5,868,322 | A | 2/1999 | Loucks, Jr. et al. |
| 5,882,680 | A | 3/1999 | Suzuki et al. |
| 5,935,331 | A | 8/1999 | Naka et al. |
| 5,942,443 | A | 8/1999 | Parce et al. |
| 5,980,936 | A | 11/1999 | Krafft et al. |
| 6,046,056 | A | 4/2000 | Parce et al. |
| 6,116,516 | A | 9/2000 | Ganan-Calvo |
| 6,119,953 | A | 9/2000 | Ganan-Calvo et al. |
| 6,120,666 | A | 9/2000 | Jacobson et al. |
| 6,130,098 | A | 10/2000 | Handique et al. |
| 6,149,789 | A | 11/2000 | Benecke et al. |
| 6,150,180 | A | 11/2000 | Parce et al. |
| 6,174,469 | B1 | 1/2001 | Ganan-Calvo |
| 6,177,479 | B1 | 1/2001 | Nakajima et al. |
| 6,187,214 | B1 | 2/2001 | Ganan-Calvo |
| 6,189,803 | B1 | 2/2001 | Ganan-Calvo |
| 6,196,525 | B1 | 3/2001 | Ganan-Calvo |
| 6,197,835 | B1 | 3/2001 | Ganan-Calvo |
| 6,221,654 | B1 | 4/2001 | Quake et al. |
| 6,227,466 | B1 | 5/2001 | Hartman et al. |
| 6,234,402 | B1 | 5/2001 | Ganan-Calvo |
| 6,241,159 | B1 | 6/2001 | Ganan-Calvo et al. |
| 6,248,378 | B1 | 6/2001 | Ganan-Calvo |
| 6,252,129 | B1 | 6/2001 | Coffee |
| 6,267,858 | B1 | 7/2001 | Parce et al. |
| 6,274,337 | B1 | 8/2001 | Parce et al. |
| 6,296,020 | B1 | 10/2001 | McNeely et al. |
| 6,299,145 | B1 | 10/2001 | Ganan-Calvo |
| 6,301,055 | B1 | 10/2001 | Legrand et al. |
| 6,306,659 | B1 | 10/2001 | Parce et al. |
| 6,355,198 | B1 | 3/2002 | Kim et al. |
| 6,357,670 | B2 | 3/2002 | Ganan-Calvo |
| 6,386,463 | B1 | 5/2002 | Ganan-Calvo |
| 6,394,429 | B2 | 5/2002 | Ganan-Calvo |
| 6,399,389 | B1 | 6/2002 | Parce et al. |
| 6,405,936 | B1 | 6/2002 | Ganan-Calvo |
| 6,408,878 | B2 | 6/2002 | Unger et al. |
| 6,429,025 | B1 | 8/2002 | Parce et al. |
| 6,432,148 | B1 | 8/2002 | Ganan-Calvo |
| 6,432,630 | B1 | 8/2002 | Blankenstein |
| 6,450,189 | B1 | 9/2002 | Ganan-Calvo |
| 6,464,886 | B2 | 10/2002 | Ganan-Calvo |
| 6,479,299 | B1 * | 11/2002 | Parce et al. .......... B01J 19/0093 204/450 |
| 6,489,103 | B1 | 12/2002 | Griffiths et al. |
| 6,506,609 | B1 | 1/2003 | Wada et al. |
| 6,508,988 | B1 | 1/2003 | Van Dam et al. |
| 6,520,425 | B1 | 2/2003 | Reneker |
| 6,540,895 | B1 | 4/2003 | Spence et al. |
| 6,554,202 | B2 | 4/2003 | Gañán-Calvo |
| 6,557,834 | B2 | 5/2003 | Gañan-Cálvo |
| 6,558,944 | B1 | 5/2003 | Parce et al. |
| 6,558,960 | B1 | 5/2003 | Parce et al. |
| 6,560,030 | B2 | 5/2003 | Legrand et al. |
| 6,592,821 | B1 | 7/2003 | Wada et al. |
| 6,608,726 | B2 | 8/2003 | Legrand et al. |
| 6,610,499 | B1 | 8/2003 | Fulwyler et al. |
| 6,614,598 | B1 | 9/2003 | Quake et al. |
| 6,630,353 | B1 | 10/2003 | Parce et al. |
| 6,645,432 | B1 | 11/2003 | Anderson et al. |
| 6,660,252 | B2 | 12/2003 | Matathia et al. |
| 6,752,922 | B2 | 6/2004 | Huang et al. |
| 6,790,328 | B2 | 9/2004 | Jacobson et al. |
| 6,806,058 | B2 | 10/2004 | Jesperson et al. |
| 6,890,487 | B1 | 5/2005 | Sklar et al. |
| 6,911,132 | B2 * | 6/2005 | Pamula et al. ................. 204/600 |
| 6,935,768 | B2 | 8/2005 | Löwe et al. |
| 7,041,481 | B2 | 5/2006 | Anderson et al. |
| 7,068,874 | B2 | 6/2006 | Wang et al. |
| 7,115,230 | B2 | 10/2006 | Sundararajan et al. |
| 7,204,431 | B2 | 4/2007 | Li et al. |
| 7,268,167 | B2 | 9/2007 | Higuchi et al. |
| 7,294,503 | B2 | 11/2007 | Quake et al. |
| 7,655,470 | B2 | 2/2010 | Ismagilov et al. |
| 7,704,457 | B2 * | 4/2010 | Patton ................... B01F 5/0646 422/63 |
| 7,708,949 | B2 | 5/2010 | Stone et al. |
| RE41,780 | E | 9/2010 | Anderson et al. |
| 7,897,044 | B2 | 3/2011 | Hoyos et al. |
| 7,901,939 | B2 | 3/2011 | Ismagliov et al. |
| 7,955,864 | B2 * | 6/2011 | Cox et al. ......... B01L 3/502715 137/565.01 |
| 7,968,287 | B2 | 6/2011 | Griffiths et al. |
| 8,287,711 | B2 | 10/2012 | Pollack et al. |
| 8,337,778 | B2 | 12/2012 | Stone et al. |
| 8,622,987 | B2 | 1/2014 | Ismagilov et al. |
| 8,663,561 | B2 * | 3/2014 | Patton ................... B01F 5/0646 250/372 |
| 8,765,485 | B2 | 7/2014 | Link et al. |
| 8,871,444 | B2 | 10/2014 | Griffiths et al. |
| 8,986,628 | B2 | 3/2015 | Stone et al. |
| 9,038,919 | B2 | 5/2015 | Link et al. |

(56) References Cited

U.S. PATENT DOCUMENTS

| | | | |
|---|---|---|---|
| 9,364,803 B2* | 6/2016 | Yurkovetsky et al. | B01F 5/0471 |
| 2001/0048637 A1 | 12/2001 | Weigl et al. | |
| 2001/0050881 A1 | 12/2001 | Depaoli et al. | |
| 2002/0004532 A1 | 1/2002 | Matathia et al. | |
| 2002/0008028 A1 | 1/2002 | Jacobson et al. | |
| 2002/0058332 A1 | 5/2002 | Quake et al. | |
| 2002/0119459 A1 | 8/2002 | Griffiths | |
| 2002/0130044 A1 | 9/2002 | Rossier et al. | |
| 2002/0150512 A1 | 10/2002 | Kellogg et al. | |
| 2003/0015425 A1 | 1/2003 | Bohm et al. | |
| 2003/0027426 A1 | 2/2003 | Milligan et al. | |
| 2003/0039169 A1 | 2/2003 | Ehrfeld et al. | |
| 2003/0085719 A1 | 5/2003 | Yoon et al. | |
| 2003/0124586 A1 | 7/2003 | Griffiths et al. | |
| 2003/0183525 A1 | 10/2003 | Elrod et al. | |
| 2004/0007463 A1* | 1/2004 | Ramsey et al. | B01F 5/0471 204/450 |
| 2004/0027915 A1 | 2/2004 | Lowe et al. | |
| 2004/0031688 A1 | 2/2004 | Shenderov | |
| 2004/0096515 A1 | 5/2004 | Bausch et al. | |
| 2004/0182712 A1 | 9/2004 | Basol | |
| 2005/0032238 A1 | 2/2005 | Karp et al. | |
| 2005/0032240 A1 | 2/2005 | Lee et al. | |
| 2005/0087122 A1* | 4/2005 | Ismagliov et al. | B01F 5/0646 117/2 |
| 2005/0103690 A1 | 5/2005 | Kawano et al. | |
| 2005/0172476 A1 | 8/2005 | Stone et al. | |
| 2005/0183995 A1 | 8/2005 | Deshpande et al. | |
| 2005/0207940 A1 | 9/2005 | Butler et al. | |
| 2005/0221339 A1 | 10/2005 | Griffiths et al. | |
| 2005/0272159 A1* | 12/2005 | Ismagilov et al. | B01F 5/0646 436/34 |
| 2006/0003439 A1* | 1/2006 | Ismagilov et al. | B01F 5/0471 435/287.2 |
| 2006/0051329 A1 | 3/2006 | Lee et al. | |
| 2006/0078888 A1 | 4/2006 | Griffiths et al. | |
| 2006/0078893 A1 | 4/2006 | Griffiths et al. | |
| 2006/0108012 A1 | 5/2006 | Barrow et al. | |
| 2006/0163385 A1 | 7/2006 | Link et al. | |
| 2006/0169800 A1 | 8/2006 | Rosell et al. | |
| 2006/0263888 A1 | 11/2006 | Fritz et al. | |
| 2007/0003442 A1 | 1/2007 | Link et al. | |
| 2007/0045117 A1 | 3/2007 | Pamula et al. | |
| 2007/0054119 A1 | 3/2007 | Garstecki et al. | |
| 2007/0056853 A1 | 3/2007 | Aizenberg et al. | |
| 2007/0092914 A1 | 4/2007 | Griffiths et al. | |
| 2007/0172873 A1 | 7/2007 | Brenner et al. | |
| 2007/0195127 A1 | 8/2007 | Ahn et al. | |
| 2008/0003142 A1 | 1/2008 | Link et al. | |
| 2008/0004436 A1 | 1/2008 | Tawfik et al. | |
| 2008/0014589 A1 | 1/2008 | Link et al. | |
| 2008/0023330 A1 | 1/2008 | Viovy et al. | |
| 2009/0012187 A1 | 1/2009 | Chu et al. | |
| 2009/0068170 A1 | 3/2009 | Weitz et al. | |
| 2009/0131543 A1 | 5/2009 | Weitz et al. | |
| 2010/0022414 A1 | 1/2010 | Link et al. | |
| 2010/0130369 A1 | 5/2010 | Shenderov et al. | |
| 2010/0137163 A1 | 6/2010 | Link et al. | |
| 2010/0172803 A1 | 7/2010 | Stone et al. | |
| 2010/0173394 A1 | 7/2010 | Colston, Jr. et al. | |
| 2012/0015382 A1 | 1/2012 | Weitz et al. | |
| 2014/0037514 A1 | 2/2014 | Stone et al. | |
| 2015/0283546 A1 | 10/2015 | Link et al. | |
| 2016/0097087 A1* | 4/2016 | Wiyatno et al. | G01N 27/44769 435/6.12 |

FOREIGN PATENT DOCUMENTS

| | | |
|---|---|---|
| CH | 1 446 998 | 8/1976 |
| CN | 1344173 A | 4/2002 |
| CN | 1400100 A | 3/2003 |
| DE | 43 08 839 A1 | 9/1994 |
| DE | 4438232 A1 | 5/1996 |
| DE | 199 61 257 A1 | 7/2001 |
| DE | 100 15 109 A1 | 10/2001 |
| DE | 100 41 823 A1 | 3/2002 |
| EP | 0 249 007 A2 | 12/1987 |
| EP | 0 718 038 B1 | 10/2002 |
| EP | 1 362 634 A1 | 11/2003 |
| EP | 1 741 482 A2 | 1/2007 |
| GB | 2 097 692 A | 11/1982 |
| JP | S52-144372 A | 12/1977 |
| JP | 53-072016 A | 6/1978 |
| JP | S62-254830 A | 11/1987 |
| JP | 3-232525 | 10/1991 |
| JP | H03-292881 A | 12/1991 |
| JP | H08-071489 A | 3/1996 |
| JP | 8-153669 | 6/1996 |
| JP | 10-217477 | 8/1998 |
| JP | H10-509434 A | 9/1998 |
| JP | H11-276802 A | 10/1999 |
| JP | 2000-512893 A | 10/2000 |
| JP | 2001-515204 A | 9/2001 |
| JP | 2001-301154 | 10/2001 |
| JP | 2001-517353 A | 10/2001 |
| JP | 2001-520186 A | 10/2001 |
| JP | 2002-503336 A | 1/2002 |
| JP | 2002-528301 A | 9/2002 |
| JP | 2002-533084 A | 10/2002 |
| JP | 2003-501257 A | 1/2003 |
| JP | 2003-504171 A | 2/2003 |
| JP | 2003-507162 A | 2/2003 |
| JP | 2003-514221 A | 4/2003 |
| JP | 2003-202321 A | 7/2003 |
| JP | 2005-037346 A | 2/2005 |
| JP | 2010-198393 A | 9/2010 |
| WO | WO 91/07772 A1 | 5/1991 |
| WO | WO 96/29629 A2 | 9/1996 |
| WO | WO 97/23140 A1 | 7/1997 |
| WO | WO 97/28556 | 8/1997 |
| WO | WO 97/49484 A1 | 12/1997 |
| WO | WO 98/52691 A1 | 11/1998 |
| WO | WO 99/12016 A1 | 3/1999 |
| WO | WO 99/20253 A1 | 4/1999 |
| WO | WO 99/47273 A2 | 9/1999 |
| WO | WO 99/61888 A2 | 12/1999 |
| WO | WO 00/24584 A1 | 5/2000 |
| WO | WO 00/32307 A1 | 6/2000 |
| WO | WO 00/37648 A1 | 6/2000 |
| WO | WO 00/47322 A2 | 8/2000 |
| WO | WO 00/52455 A1 | 9/2000 |
| WO | WO 00/54735 A1 | 9/2000 |
| WO | WO 00/54845 A1 | 9/2000 |
| WO | WO 00/70080 A1 | 11/2000 |
| WO | WO 00/76673 A1 | 12/2000 |
| WO | WO 01/12327 A1 | 2/2001 |
| WO | WO 01/34302 A2 | 5/2001 |
| WO | WO 01/68257 A1 | 9/2001 |
| WO | WO 01/69289 A2 | 9/2001 |
| WO | WO 01/72431 | 10/2001 |
| WO | WO 01/80283 A1 | 10/2001 |
| WO | WO 01/89787 A2 | 11/2001 |
| WO | WO 01/89788 A2 | 11/2001 |
| WO | WO 01/94635 A2 | 12/2001 |
| WO | WO 02/13786 A2 | 2/2002 |
| WO | WO 02/16017 A2 | 2/2002 |
| WO | WO 02/18949 A2 | 3/2002 |
| WO | WO 02/22878 A1 | 3/2002 |
| WO | WO 02/47665 A2 | 6/2002 |
| WO | WO 02/48177 A1 | 6/2002 |
| WO | WO 02/060275 | 8/2002 |
| WO | WO 02/060591 | 8/2002 |
| WO | WO 02/064243 A1 | 8/2002 |
| WO | WO 02/068104 | 9/2002 |
| WO | WO 02/068104 A1 | 9/2002 |
| WO | WO 02/103011 A2 | 12/2002 |
| WO | WO 03/011443 A2 | 2/2003 |
| WO | WO 2004/002627 A2 | 1/2004 |
| WO | WO 2004/002627 A3 | 1/2004 |
| WO | WO 2004/038363 A2 | 5/2004 |
| WO | WO 2004/071638 A2 | 8/2004 |
| WO | WO 2004/091763 A2 | 10/2004 |

(56) References Cited

FOREIGN PATENT DOCUMENTS

| | | |
|---|---|---|
| WO | WO 2004/102204 A1 | 11/2004 |
| WO | WO 2004/103565 A2 | 12/2004 |
| WO | WO 2005/002730 A1 | 1/2005 |
| WO | WO 2005/021151 A1 | 3/2005 |
| WO | WO 2005/049787 A2 | 6/2005 |
| WO | WO 2005/103106 A1 | 11/2005 |
| WO | WO 2006/002641 A1 | 1/2006 |
| WO | WO 2006/078841 A1 | 7/2006 |
| WO | WO 2006/096571 A2 | 9/2006 |
| WO | WO 2006/101851 A2 | 9/2006 |
| WO | WO 2007/081385 A2 | 7/2007 |
| WO | WO 2007/089541 A2 | 8/2007 |
| WO | WO 2007/114794 A1 | 10/2007 |
| WO | WO 2007/133710 A2 | 11/2007 |
| WO | WO 2007/138178 A2 | 12/2007 |
| WO | WO 2008/121342 A2 | 10/2008 |
| WO | WO 2008/134153 A1 | 11/2008 |
| WO | WO 2012/048341 A1 | 4/2012 |
| WO | WO 2013/177220 A1 | 11/2013 |

OTHER PUBLICATIONS

Japanese Office Action for Application No. JP 2009-231040 dated Jul. 1, 2014.
Office Action dated Jun. 10, 2014 for U.S. Appl. No. 11/246,911.
Office Action dated Jun. 5, 2014 for U.S. Appl. No. 13/679,190.
Advisory Action dated Sep. 9, 2014 for U.S. Appl. No. 13/679,190.
Ghadessy et al. Directed evolution of polymerase function by compartmentalized self-replication. Proc Natl Acad Sci USA. Apr. 10, 2001; 98(8):4552-7. Epub Mar. 27, 2001.
Hug et al. Measurement of the number of molecules of a single mRNA species in a complex mRNA preparation. J Theor Biol. Apr. 21, 2003; 221(4):615-24.
Ahn, K., et al., Dielectrophoretic manipulation of drops for high-speed microfluidic sorting devices. App Phys Lett. Feb. 2006;88(2):024104-1-024104-3.
Ando, S., et al., PLGA microspheres containing plasmid DNA: preservation of supercoiled DNA via cryopreparation and carbohydrate stabilization. J Pharm Sci. Jan. 1999;88(1):126-30.
Anna, S.L., et al., Formation of dispersions using "flow focusing" in microchannels. App Phys Lett. Jan. 2003;82(3):364-6.
Benichou, A., et al., "Double Emulsions Stabilized by New Molecular Recognition Hybrids of Natural Polymers," Polym. Adv. Tehcnol., vol. 13, pp. 1019-1031 (2002). Month not cited on publication.
Bibette, J., et al., "Emulsions: basic principles", Rep. Prog. Phys.. 62 (1999) 969-1033. The year of publication is sufficiently earlier than the effective U.S. filed and any foreign priority date so that the particular month of publication is not in issue. See MPEP 609.04(a).
Chao, W., et al., "Control of Concentration and Volume Gradients in Microfluidic Droplet Arrays for Protein Crystallization Screening", 26th Annual International Conference of the IEEE Engineering in Medicine and Biology Society, Sep. 1-5, 2004, Francisco, California.
Chao, W., et al., "Droplet Arrays in Microfluidic Channels for Combinatorial Screening Assays", Hilton Head 2004: A Solid State Sensor, Actuator and Microsystems Workshop, Hilton Head Island, South Carolina, Jun. 6-10, 2004.
Chen, C.C., et al., "Microfluidic Switch for Embryo and Cell Sorting," The 12th International Conference on Solid State Sensors, Actuators, and Microsystems, Boston, MA Jun. 8-12, 2003 Transducers, vol. 1, pp. 659-662 (2003).
Chen, L.X., et al., Capturing a photoexcited molecular structure through time-domain x-ray absorption fine structure. Science. Apr. 13, 2001;292(5515):262-4.
Cheng, Z., et al., "Electro flow focusing in microfluidic devices," Microfluidics Poster, presented at DEAS, "Frontiers in Nanoscience," presented Apr. 10, 2003.

Chiba, M., et al., Controlled protein delivery from biodegradable tyrosine-containing poly(anhydride-co-imide) microspheres. Biomaterials. Jul. 1997;18(13):893-901.
Cohen, S., et al., Controlled delivery systems for proteins based on poly(lactic/glycolic acid) microspheres. Pharm Res. Jun. 1991;8(6):713-20.
Collins, J., et al., Microfluidic flow transducer based on the measurement of electrical admittance. Lab Chip. Feb. 2004;4(1):7-10. Epub Nov. 11, 2003.
Collins, J., et al., "Optimization of Shear Driven Droplet Generation in a Microfluidic Device", ASME International Mechanical Engineering Congress and R&D Expo, Nov. 2003, Washington.
Cortesi, R., et al., Production of lipospheres as carriers for bioactive compounds. Biomaterials. Jun. 2002;23(11):2283-94.
Dinsmore, A.D., et al., "Colloidosomes: Selectively Permeable Capsules Composed of Colloidal Particles", Science, Nov. 2002, 298:1006-1009.
Dinsmore, A.D., et al., "Colloidosomes: Selectively-Permeable Capsules Composed of Colloidal Particles", Supplementary Material. Available at http://www.sciencemag.org/content/suppl/2002/10/30/298.5595.1006.DC1/Dinsmore.pdf. Nov. 2002.
Dove, A., et al., Nature Biotechnology, Dec. 2002, 20:1213.
Edris, A., et al., Encapsulation of orange oil in a spray dried double emulsion. Nahrung. Apr. 2001;45(2):133-7.
Eow, J.S., et al., Electrostatic and hydrodynamic separation of aqueous drops in a flowing viscous oil. Chemical Engineering and Processing. Sep. 2002;41:649-57.
Eow, J.S., et al., Electrocoalesce-separators for the separation of aqueous drops from a flowing dielectric viscous liquid. Separation and Purification Technology. Oct. 2002;29:63-77.
Eow, J.S., et al., Electrostatic enhancement of coalescence of water droplets in oil: a review of the technology. Chemical Engineering Journal. Jan. 2002;85:357-68.
Eow, J.S., et al., Motion, deformation and break-up of aqueous drops in oils under high electric field strengths. Chemical Engineering and Processing. Apr. 2003;42:259-72.
Eow, J.S., et al., the bahaviour of a liquid-liquid interface and drop-interface coalescence under the influence of an electric field. Colloids and Surfaces A: Physiochem. Eng. Aspects. Mar. 2003:101-23.
Fisher, J.S., et al., "Cell Encapsulation on a Microfluidic Platform," The Eighth International Conference on Miniaturised Systems for Chemistry and Life Sciences, MicroTAS 2004, Sep. 26-30, Malmo, Sweden.
Fu, A.Y., et al., A microfabricated fluorescence-activated cell sorter. Nat Biotechnol. Nov. 1999;17(11):1109-11.
Gallarate, M., et al., On the stability of ascorbic acid in emulsified systems for topical and cosmetic use. Int J Pharm. Oct. 25, 1999;188(2):233-41.
Ganan-Calvo, A., Generation of Steady Liquid Microthreads and MicronSized Monodisperse Sprays in Gas Streams. Phys Rev Lett. Jan. 1998;80(2):285-8.
Ganan-Calvo, A.M., "Perfectly monodisperse micro-bubble production by novel mechanical means. Scaling laws," American Physical Society 53rd Annual Meeting of the Division of Fluid Dynamics, Nov. 19-21, 2000.
Ganan-Calvo, A.M., Perfectly monodisperse microbubbling by capillary flow focusing. Phys Rev Lett. Dec. 31, 2001;87(27 Pt 1):274501. Epub Dec. 11, 2001.
Grasland-Mongrain, et al., "Droplet coalescence in microfluidic devices," Jan.-Jul. 2003, pp. 1-30.
Griffiths, A., et al., Man-made enzymes—from design to in vitro compartmentalisation. Curr Opin Biotechnol. Aug. 2000;11(4):338-53.
Griffiths, A.D. et al., "Miniaturising the laboratory in emulsion droplets," Trend Biotech, 12:1-8, 2006. Month not cited on publication.
Hadd, A.G., et al., Microchip device for performing enzyme assays. Anal Chem. Sep. 1, 1997;69(17):3407-12.
Hanes, J., et al., Degradation of porous poly(anhydride-co-imide) microspheres and implications for controlled macromolecule delivery. Biomaterials. Jan.-Feb. 1998;19(1-3):163-72.

(56) References Cited

OTHER PUBLICATIONS

Hayward, R.C., et al., Dewetting instability during the formation of polymersomes from block-copolymer-stabilized double emulsions. Langmuir. May 9, 2006;22(10):4457-61.
Hung, L.H., et al., "Controlled Droplet Fusion in Microfluidic Devices", MicroTAS Sep. 26-30, 2004, Malmo, Sweden.
Hung, L.H., et al., "Optimization of Droplet Generation by controlling PDMS Surface Hydrophobicity," 2004 ASME International Mechanical Engineering Congres and RD&D Expo, Nov. 13-19, 2004, Anaheim, CA.
Jang, J.H., et al., Controllable delivery of non-viral DNA from porous scaffolds. J Control Release. Jan. 9, 2003;86(1):157-68.
Jo, Y.S., et al, Encapsulation of Bovine Serum Albumin in Temperature-Programmed "Shell-in-Shell" Structures. Macromol. Rapid Commun. Nov. 2003;24:957-62.
Kanouni, M., et al., Preparation of a stable double emulsion (W1/O/W2): role of the interfacial films on the stability of the system. Adv Colloid Interface Sci. Dec. 2, 2002;99(3):229-54.
Kim, H.K., et al., Comparative study on sustained release of human growth hormone from semi-crystalline poly(L-lactic acid) and amorphous poly(D,L-lactic-co-glycolic acid) microspheres: morphological effect on protein release. J Control Release. Jul. 23, 2004;98(1):115-25.
Lamprecht, A., et al., pH-sensitive microsphere delivery increases oral bioavailability of calcitonin. J Control Release. Jul. 23, 2004;98(1):1-9.
Leary, J.F., et al., "Application of Advanced Cytometric and Molecular Technologies to Minimal Residual Disease Monitoring," Proceedings of SPIE, vol. 3913, pp. 36-44 (2000). The year of publication is sufficiently earlier than the effective U.S. filed and any foreign priority date so that the particular month of publication is not in issue. See MPEP 609.04(a).
Lee, D.H., et al., Effective Formation of Silicone-in-Fluorocarbon-in-Water Double Emulsions: Studies on Droplet Morphology and Stability. Journal of Dispersion Science and Technology. Feb. 2002;23(4):491-7.
Lee, M.H., et al., Preparation of Silica Particles Encapsulating Retinol Using O/W/O Multiple Emulsions. J of Coll Inter Sci. Jun. 2001;240:83-9.
Lemoff, A.V., et al., An AC Magnetohydrodynamic Microfluidic Switch for Micro Total Analysis Systems. Biomed Microdev. Mar. 2003;5(1):55-60.
Link, D.R., et al.,Geometrically mediated breakup of drops in microfluidic devices. Phys Rev Lett. Feb. 6, 2004;92(5):054503. Epub Feb. 6, 2004.
Lopez-Herrera, J.M., et al., Coaxial jets generated from electrified Taylor cones. Scaling laws. Aerosol Sci. May 2003;34 (5):535-552.
Lopez-Herrera, J.M., et al., One-Dimensional Simulation of the Breakup of Capillary Jets of Conducting Liquids. Application to E.H.D. Spraying. J Aerosol Sci. Aug. 1999;30(7):895-912.
Lopez-Herrera, J.M., et al., the electrospraying of viscous and non-viscous semi-insulating liquids. Scalilng laws. Bulletin of the American Physical Society. Nov. 1995;40(12):2041.
Lorenceau, E., et al., Generation of polymerosomes from double-emulsions. Langmuir. Sep. 27, 2005;21(20):9183-6.
Loscertales, I.G., et al.,Micro/nano encapsulation via electrified coaxial liquid jets. Science. Mar. 1, 2002;295(5560):1695-8.
Lundstrom, Kenneth, et al., "Breakthrough in cancer therapy: Encapsulation of drugs and viruses", www.currentdrugdiscovery.com, Nov. 2002, 19-23.
Marques, F., et al., Porous Flow within Concentric Cylinders. Bulletin of the American Physical Society Division of Fluid Dynamics Nov. 1996;41:1768.
Molecular Probes, ATP Determination Kit (A-22066) (2003). Revised Apr. 23, 2003.
Nakano, M., et al., Single-molecule PCR using water-in-oil emulsion. J Biotechnol. Apr. 24, 2003;102(2):117-24.
Nihant, N., et al., Polylactide microparticles prepared by double emulsion/evaporation technique. I. Effect of primary emulsion stability. Pharm Res. Oct. 1994;11(10):1479-84.
Nisisako, T. et al., Controlled formulation of monodisperse double emulsions in a multiple-phase microfluidic system. Soft Matter. Apr. 2005;1:23-7.
Nof, M., et al., Drug-releasing scaffolds fabricated from drug-loaded microspheres. J Biomed Mater Res. Feb. 2002;59(2):349-56.
Oh, C., et al., Distribution of macropores in silica particles prepared by using multiple emulsions. J Colloid Interface Sci. Oct. 1, 2002;254(1):79-86.
Okushima, S., et al,. Controlled production of monodisperse double emulsions by two-step droplet breakup in microfluidic devices. Langmuir. Nov. 9, 2004;20(23):9905-8.
Ouellette, J., "A New Wave of Microfluidic Device," The Industrial Physicist, pp. 14-17, Aug./Sep. 2003.
Piemi, M.P.Y., et al., Transdermal delivery of glucose through hairless rat skin in vitro: effect of multiple and simple emulsions. International Journal of Pharmeceutics. Sep. 1998;171(2):207-215.
Priest, C. et al., Generation of Monodisperse Gel Emulsions in a Microfluidic Device. Appl Phys Lett. Jan. 2006;88:024106.
Raghuraman, B., et al., Emulsion liquid membranes for wastewater treatment: equilibrium models for some typical metal-extractant systems. Environ Sci Technol. Jun. 1, 1994;28(6):1090-8.
Schubert, C., et al., Designer Capsules. Nature Medicine. Dec. 2002;8(12):1362.
Silva-Cunha, A., et al., W/O/W multiple emulsions of insulin containing a protease inhibitor and an absorption enhancer: biological activity after oral administration to normal and diabetic rats. International Journal of Pharmaceutics. Jun. 1998;169:33-44.
Sohn, L.L., et al., Capacitance cytometry: measuring biological cells one by one. Proc Natl Acad Sci U S A. Sep. 26, 2000;97(20):10687-90.
Song, H., et al., A microfluidic system for controlling reaction networks in time. Angew Chem Int Ed Engl. Feb. 17, 2003;42(7):768-72.
Sugiura, S., et al., Interfacial Tension Driven Monodispersed Droplet Formation from Microfabricated Channel Array. Langmuir. Aug. 2001;17:5562-6.
Takeuchi, S., et al., An Axisymmetric Flow-Focusing Microfluidic Device, Adv. Mater. Apr. 2005;17(8):1067-72.
Tan, Y.C., "Microfluidic Liposome Generation from Monodisperse Droplet Emulsion-Towards the Realization of Artificial Cells", Summer Bioengineering Conference, Jun. 2003, Florida.
Tan, Y.C., "Monodisperse Droplet Emulsions in Co-Flow Microfluidic Channels", Micro TAS 2003, Lake Tahoe. Month not cited on publication.
Tan, Y.C., et al., "Controlled Fission of Droplet Emulsions in Bifurcating Microfluidic Channels", Transducers 2003, Boston. Month not cited on publication.
Tan, Y.C., et al., Design of microfluidic channel geometries for the control of droplet volume, chemical concentration, and sorting. Lab Chip. Jul. 2004;4:292-8.
Tawfik, D.S., et al., Man-made cell-like compartments for molecular evolution. Nature Biotechnology. Jul. 1998;16:652-6.
Terray, A., et al, Fabrication of linear colloidal structures for microfluidic applications. Applied Physics Letters. Aug. 2002;81(9):1555-1557.
Terray, A., et al., Microfluidic Control Using Colloidal Devices. Science. Jun. 2002;296:1841-4.
Thorsen, T., et al., Dynamic Pattern Formation in a Vesicle-Generating Microfluidic Device. Physical Review Letters. Apr. 2001;86(18):4163-6.
Umbanhowar, P.B., et al., Monodisperse Emulsion Generation via Drop Break Off in a Coflowing Stream. Langmuir. Jan. 2000;16(2):347-51.
Utada, A.S., et al., Monodisperse Double Emulsions Generated from a Microcapillary Device. Science. Apr. 2005;308:537-41.
Web page, Experimental Soft Condensed Matter Group, "Cool Picture of the Moment" Harvard University, Prof. D. A. Weitz. Dated Nov. 2, 2009.
Wolff, A., et al., Integrating advanced functionality in a microfabricated high-throughput fluorescent-activated cell sorter. Lab Chip. Jan. 2003;3:22-7.

(56) References Cited

OTHER PUBLICATIONS

Xu, S., et al., "Generation of Monodisperse Particles by Using Microfluidics: Control over Size, Shape and Composition," Angew. Chem. Int. Ed., vol. 43, pp. 2-5 (2004). Month not cited on publication.
Yamaguchi, Y., et al., Insulin-loaded biodegradable PLGA microcapsules: initial burst release controlled by hydrophilic additives. J Control Release. Jun. 17, 2002;81(3):235-49.
Zhang, J.H., et al., A Simple Statistical Parameter for Use in Evaluation and Validation of High Throughput Screening Assays. J Biomol Screen. Apr. 1999;4(2):67-73.
Zheng, B., et al., A microfluidic approach for screening submicroliter volumes against multiple reagents by using preformed arrays of nanoliter plugs in a three-phase liquid/liquid/gas flow. Angew Chem Int Ed Engl. Apr. 22, 2005;44(17):2520-3.
Zimmermann, U., et al., Microscale production of hybridomas by hypo-osmolar electrofusion. Hum Antibodies Hybridomas. Jan. 1992;3(1):14-8.
Lopez-Herrera, Journal of Aerosol Science, vol. 30, No. 7. 1999. pp. 895-912.
Lopez-Herrera, Journal of Aerosol Science, vol. 34. No. 5. 2003. pp. 535-552.
Extended European Search Report for EP 08165420.4 dated Nov. 3, 2009.
Extended European Search Report for EP 10181911.8 dated Jun. 1, 2011.
Examination Report for EP 10181911.8 dated May 7, 2012.
Japanese Office Action for JP 2006-509830 dated Jun. 1, 2011.
Japanese Office Action dated Jun. 14, 2012 for JP 2006-509830.
Japanese Office Action dated Jun. 4, 2012 for JP 2010-198393.
Japanese Office Action for Application No. JP 2010-198393 dated Jul. 31, 2013 for JP 2010-198393.
International Search Report and Written Opinion dated Dec. 20, 2004 in PCT/US2004/010903.
International Preliminary Report on Patentability dated Oct. 14, 2005 in PCT/US2004/010903.
Chinese Office Communication dated Oct. 10, 2011 for CN 201010599933.9.
Chinese Office Communication dated Aug. 8, 2012 for CN 201010599933.9.
Summons to attend oral proceedings dated Mar. 7, 2012 for EP 03762228.9.
Extended European Search Report for EP 10184514.7 dated Dec. 20, 2010.
European Office Action dated Jun. 25, 2013 for EP 10184514.7.
Japanese Office Communication dated Nov. 2, 2011 for JP 2004-549845.
Japanese Office Communication dated Sep. 3, 2012 for JP 2009-265751.
Japanese Office Communication dated Oct. 1, 2013 for Application No. JP 2009-265751.
International Search Report dated Feb. 6, 2004 in PCT/US2003/20542.
Invitation to Pay Additional Fees dated Jun. 28, 2006 for PCT/US2006/007772.
International Search Report and Written Opinion dated Sep. 1, 2006 in PCT/US06/007772.
International Preliminary Report on Patentability dated Sep. 20, 2007 for PCT/US2006/007772.
Summons to attend oral proceedings dated Jun. 14, 2013 for EP 04782399.2.
Communication from Primary Examiner for Application No. EP 04782399.2 dated Sep. 16, 2013.
European Decision to Refuse for Application No. EP 04782399.2 dated Oct. 4, 2013.
International Search Report and Written Opinion dated Jan. 28, 2005 in PCT/US2004/027912.
International Preliminary Report on Patentability dated Feb. 27, 2006 in PCT/US2004/027912.
International Search Report and Written Opinion dated May 31, 2006 in PCT/US2006/001938.
Extended European Search Report dated Jan. 25, 2012 for European Application No. 10175562.7.
Japanese Office Action for Application No. JP 2008-552412 dated Mar. 6, 2013.
International Search Report dated Sep. 10, 2007 in PCT/US2007/002063.
International Preliminary Report on Patentability dated Jul. 29, 2008 in PCT/US2007/002063.
Extended European Search Report for Application No. EP 13165665.4 dated Nov. 22, 2013.
Extended European Search Report for Application No. EP 13165667.0 dated Nov. 22, 2013.
Japanese Office Action for Application No. JP 2010-198393 dated Nov. 18, 2013.
Japanese Office Action for Application No. JP 2009-231040 dated Dec. 24, 2013.
Office Action for U.S. Appl. No. 11/246,911 dated Nov. 8, 2007.
Office Action for U.S. Appl. No. 11/246,911 dated Jun. 3, 2008.
Office Action for U.S. Appl. No. 11/246,911 dated Dec. 18, 2008.
Office Action for U.S. Appl. No. 11/246,911 dated Feb. 25, 2010.
Office Action for U.S. Appl. No. 11/246,911 dated Feb. 8, 2011.
Office Action for U.S. Appl. No. 11/246,911 dated Apr. 19, 2013.
Office Action for U.S. Appl. No. 11/246,911 dated Dec. 31, 2013.
Office Action for U.S. Appl. No. 11/024,228 dated Dec. 14, 2007.
Office Action for U.S. Appl. No. 11/024,228 dated Jul. 9, 2008.
Office Action for U.S. Appl. No. 11/024,228 dated Dec. 11, 2008.
Office Action for U.S. Appl. No. 11/024,228 dated Jul. 13, 2009.
Office Action for U.S. Appl. No. 12/726,223 dated Aug. 4, 2010.
Office Communication dated Jan. 4, 2012 for U.S. Appl. No. 12/726,223.
Office Action for U.S. Appl. No. 13/679,190 dated Dec. 2, 2013.
Office Action for U.S. Appl. No. 11/360,845 dated Apr. 2, 2009.
Office Action for U.S. Appl. No. 11/360,845 dated Jan. 20, 2010.
Advisory Action for U.S. Appl. No. 11/360,845 dated Jun. 14, 2010.
Office Action for U.S. Appl. No. 11/360,845 dated Aug. 4, 2010.
Office Action for U.S. Appl. No. 11/360,845 dated Apr. 26, 2011.
Office Action dated Jun. 28, 2012 for U.S. Appl. No. 11/360,845.
Office Action dated Jan. 3, 2013 for U.S. Appl. No. 11/360,845.
Office Action for U.S. Appl. No. 11/360,845 dated Nov. 19, 2013.
Interview Summary for U.S. Appl. No. 11/360,845 dated Mar. 4, 2014.
Notice of Allowance for U.S. Appl. No. 11/360,845 dated Apr. 2, 2014.
Office Action for U.S. Appl. No. 11/368,263 dated Dec. 19, 2008.
Office Action for U.S. Appl. No. 11/698,298 dated Jun. 7, 2010.
Office Action for U.S. Appl. No. 11/698,298 dated Feb. 15, 2011.
Advisory Action for U.S. Appl. No. 11/698,298 dated May 20, 2011.
Office Communication dated Jun. 29, 2011 for U.S. Appl. No. 11/698,298.
Office Communication dated Feb. 16, 2012 for U.S. Appl. No. 11/698,298.
Japanese Office Action dated Jan. 27, 2015 for Application No. 2014-028635.
European Office Action dated Jan. 13, 2015 for Application No. 10184514.7.
Chinese Office Action dated May 19, 2015 for Application No. 201410160397.0.
Japanese Office Action dated Jun. 16, 2015 for Application No. JP 2014-089328.
Advisory Action dated Oct. 16, 2014 for U.S. Appl. No. 13/679,190.
Chou et al. Disposable Microdevices for DNA Analysis and Cell Sorting. Proc. Solid-State Sensor and Actuator Workshop, Hilton Head, SC. Jun. 8-11, 1998; 11-14.
Japanese Office Action for Application No. JP 2014-028635 dated Dec. 1, 2015.
Extended European Search Report dated Apr. 28, 2016 for European Application No. 15194786.8.
Japanese Office Action for Application No. JP 2014-028635 dated May 17, 2016.
Chinese Office Action for Application No. CN 201410160397.0 dated Mar. 8, 2016.

(56) References Cited

OTHER PUBLICATIONS

Chinese Notice of Grant for Application No. 201410160397.0 dated Sep. 8, 2016.
Japanese Office Action for Application No. JP 2014-089328 dated Apr. 26, 2016.
Japanese Office Action for Application No. JP 2014-028635 dated May 16, 2017.
European Office Action for EP 13165665.4 dated Jan. 31, 2017.
European Office Action for EP 13165667.0 dated Jan. 27, 2017.
Japanese Office Action for Application No. JP 2014-089328 dated Feb. 21, 2017.
Eow et al., Electrostatic enhancement of coalescence of water droplets in oil: a review of the current understanding. Chem Eng J Dec. 2001;84:173-92.
Japanese Office Action and English Translation thereof, dated Jul. 18, 2017 for JP 2016-183376.
Office Action dated Jun. 7, 2017 for U.S. Appl. No. 14/662,668.

\* cited by examiner

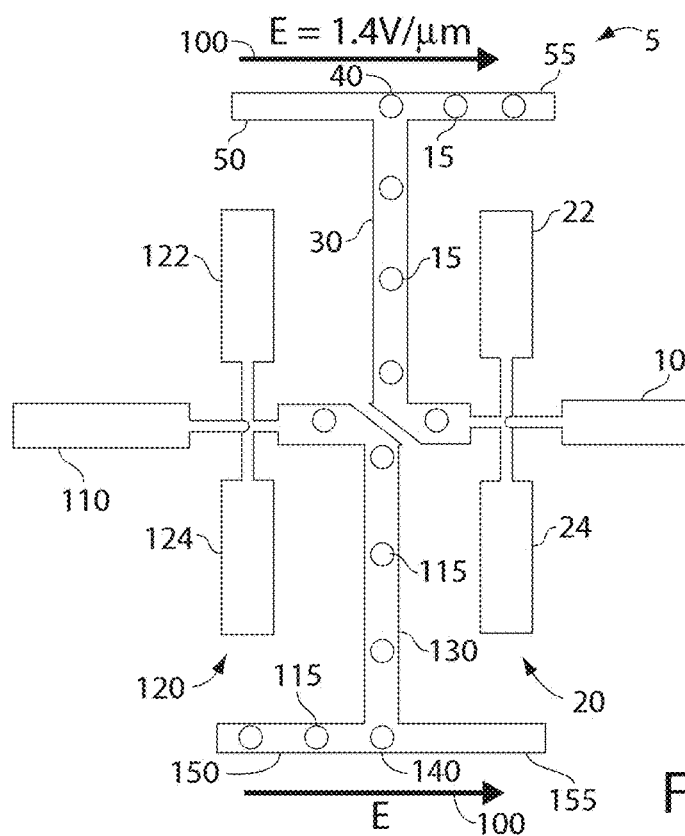
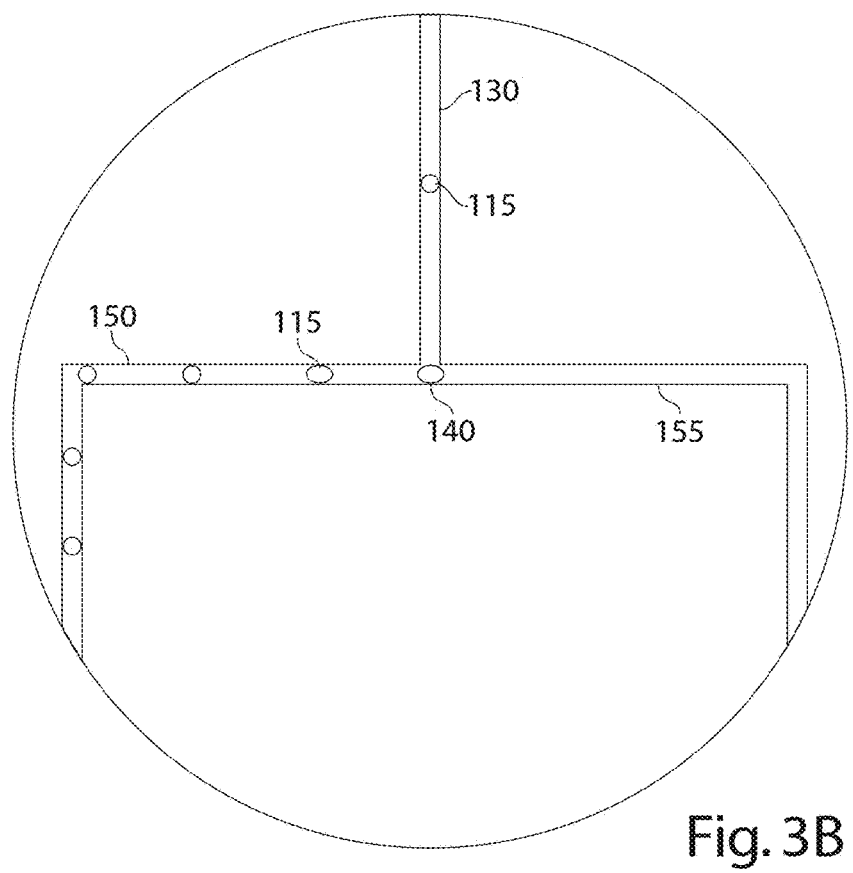
Fig. 3A
Fig. 3B

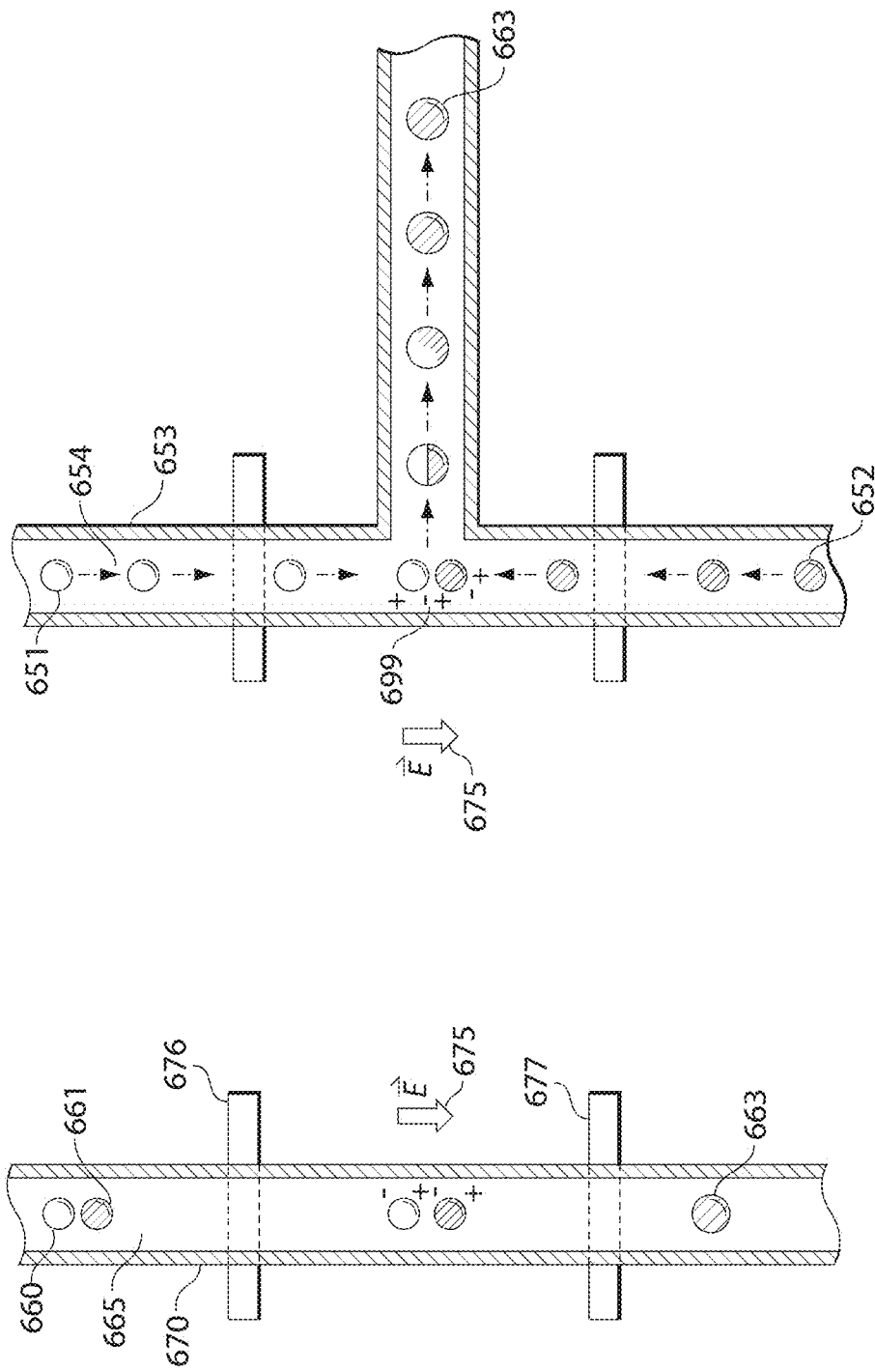

METHODS OF INTRODUCING A FLUID INTO DROPLETS

RELATED APPLICATIONS

This application is a continuation of U.S. application Ser. No. 11/360,845, filed Feb. 23, 2006, entitled "Electronic Control of Fluidic Species," which is a continuation of International Patent Application Ser. No. PCT/US2004/027912, filed Aug. 27, 2004, which claims priority to U.S. Provisional Patent Application Ser. No. 60/498,091, filed Aug. 27, 2003, entitled "Electronic Control of Fluidic Species," by Link, et al., all incorporated herein by reference.

GOVERNMENT FUNDING

Various aspects of the present invention were made with U.S. Government support under grant numbers DMR-0213805 and DMR-0243715 awarded by the National Science Foundation. The U.S. Government has certain rights in the invention.

FIELD OF INVENTION

The present invention generally relates to systems and methods for the control of fluidic species and, in particular, to systems and methods for the electronic control of fluidic species.

BACKGROUND

The manipulation of fluids to form fluid streams of desired configuration, discontinuous fluid streams, droplets, particles, dispersions, etc., for purposes of fluid delivery, product manufacture, analysis, and the like, is a relatively well-studied art. For example, highly monodisperse gas bubbles, less than 100 microns in diameter, have been produced using a technique referred to as capillary flow focusing. In this technique, gas is forced out of a capillary tube into a bath of liquid, the tube is positioned above a small orifice, and the contraction flow of the external liquid through this orifice focuses the gas into a thin jet which subsequently breaks into roughly equal-sized bubbles via capillary instability. In a related technique, a similar arrangement can be used to produce liquid droplets in air.

An article entitled "Generation of Steady Liqui-d Microthreads and Micron-Sized Monodisperse Sprays and Gas Streams," Phys. Rev. Lett., 80:2, Jan. 12, 1998 (Ganan-Calvo) describes formation of a microscopic liquid thread by a laminar accelerating gas stream, giving rise to a fine spray. An articled entitled "Dynamic Pattern Formation in a Vesicle-Generating Microfluidic Device," Phys. Rev. Lett., 86:18, Apr. 30, 2001 (Thorsen, et al.) describes formation of a discontinuous water phase in a continuous oil phase via microfluidic cross-flow by introducing water, at a "T" junction between two microfluidic channels, into flowing oil.

U.S. Pat. No. 6,120,666, issued Sep. 19, 2000, describes a microfabricated device having a fluid focusing chamber for spatially confining first and second sample fluid streams for analyzing microscopic particles in a fluid medium, for example, in biological fluid analysis. U.S. Pat. No. 6,116,516, issued Sep. 12, 2000, describes formation of a capillary microjet, and formation of a monodisperse aerosol via disassociation of the microjet. U.S. Pat. No. 6,187,214, issued Feb. 13, 2001, describes atomized particles in a size range of from about 1 to about 5 microns, produced by the interaction of two immiscible fluids. U.S. Patent No. 6,248, 378, issued Jun. 19, 2001, describes production of particles for introduction into food using a microjet and a monodisperse aerosol formed when the microjet dissociates.

Microfluidic systems have been described in a variety of contexts, typically in the context of miniaturized laboratory (e.g., clinical) analysis. Other uses have been described as well. For example, International Patent Publication No. WO 01/89789, published Nov. 29, 2001 by Anderson, et al., describes multi-level microfluidic systems that can be used to provide patterns of materials, such as biological materials and cells, on surfaces. Other publications describe microfluidic systems including valves, switches, and other components.

While significant advances have been made in dynamics at the macro- or microfluidic scale, improved techniques and the results of these techniques are needed.

SUMMARY OF THE INVENTION

The present invention relates to systems and methods for the electronic control of fluidic species. The subject matter of this invention involves, in some cases, interrelated products, alternative solutions to a particular problem, and/or a plurality of different uses of one or more systems and/or articles. In one aspect, the invention provides a method. In one set of embodiments, the method is a method of combining at least two species in a controlled manner in a microfluidic system. The method includes acts of providing a series of droplets flowing in a microfluidic system; selecting a first droplet from the series of droplets and separating the first droplet from at least some other droplets in the series of droplets (where the first droplet has a maximum cross-sectional dimension of less than about 100 microns and contains a first chemical, biological, or biochemical species), providing a second droplet separate from the series of droplets (where the second droplet has a maximum cross-sectional dimension of less than about 100 microns and contains a second chemical, biological, or biochemical species), selectively urging the first droplet and/or the second droplet toward a location where coalescence can occur and allowing the first droplet and the second droplet to coalesce into one combined droplet, and determining a reaction involving at least the first species in the first droplet and the second species in the second droplet.

The method, according to another set of embodiments, is a method of sorting droplets in a controlled manner in a microfluidic system. The method includes acts of providing a series of droplets flowing in a microfluidic system, and selecting a first droplet from the series of droplets and separating the first droplet from at least some other droplets in the series of droplets. In some cases, the first droplet has a maximum cross-sectional dimension of less than about 100 microns.

In yet another set of embodiments, the method is a method of imparting charge to one or more droplets in a microfluidic system. The method can include acts of providing a droplet in a microfluidic system, imparting a dipole moment to the droplet, and dividing the droplet, while the dipole moment is present, into at least two subdroplets, at least one of the subdroplets carrying a charge resulting from the dipole moment imparted to the primary droplet.

In still another set of embodiments, the method is a method of combining at least two droplets in a microfluidic system. The method includes acts of providing at least two droplets in a microfluidic system, exposing the droplets to an electric field thereby inducing, in the droplets, dipole moments, and coalescing the at least two droplets into a single droplet at least in part via droplet-droplet attraction due to the induced dipole moments.

The method, according to another set of embodiments, includes a step of producing a charge of at least about 10-14 C on a first fluid surrounded by a second, liquid fluid. The method, according to still another set of embodiments, includes a step of applying an electric force of at least about 10-9 N on a first fluid surrounded by a second, liquid fluid.

In yet another set of embodiments, in a first fluid comprising first droplets and second droplets, the first fluid surrounded by a second, liquid fluid, the method comprises sorting the first and second droplets at a rate of at least about 10 or at least about 100 droplets/s. In still another set of embodiments, the method includes steps of providing droplets of a first fluid surrounded by a second, liquid fluid, where the droplets have a ratio of droplets containing a first species to droplets free of the first species, and sorting the droplets to increase the ratio of droplets containing the first species to droplets free of the first species by at least a factor of about 2.

In another set of embodiments, in a first fluid comprising first droplets and second droplets where the first fluid is surrounded by a second, liquid fluid, the method comprises sorting the first and second droplets without substantially altering a flowrate of the second, liquid fluid. In yet another set of embodiments, the method includes a step of dividing a first fluidic droplet, surrounded by a second, liquid fluid, into two droplets using an electric field.

In another aspect, the invention is an article. The article, in one set of embodiments, includes a first fluidic droplet having a charge of at least about 10-14 C, surrounded by a second, liquid fluid. The article, in another set of embodiments, includes droplets comprising a first fluid surrounded by a second, liquid fluid, where at least about 90% of the droplets each consists of the same number of entities of a species.

In yet another aspect, the invention is an apparatus. According to one set of embodiments, the apparatus includes a microfluidic channel, and an electric field generator constructed and arranged to generate an electric field of at least about 1 V/micrometer within the microfluidic channel.

In still another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more applications incorporated by reference include conflicting and/or inconsistent disclosure with respect to each other, then the later-filed application shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures:

FIGS. 3A and 3B illustrate the apparatus of FIGS. 2A and 2B after the application of an electric field thereto.

FIGS. 13A-13D illustrate uncharged and charged droplets in channels, according to certain embodiments of the invention;

DETAILED DESCRIPTION

Figure 1A:
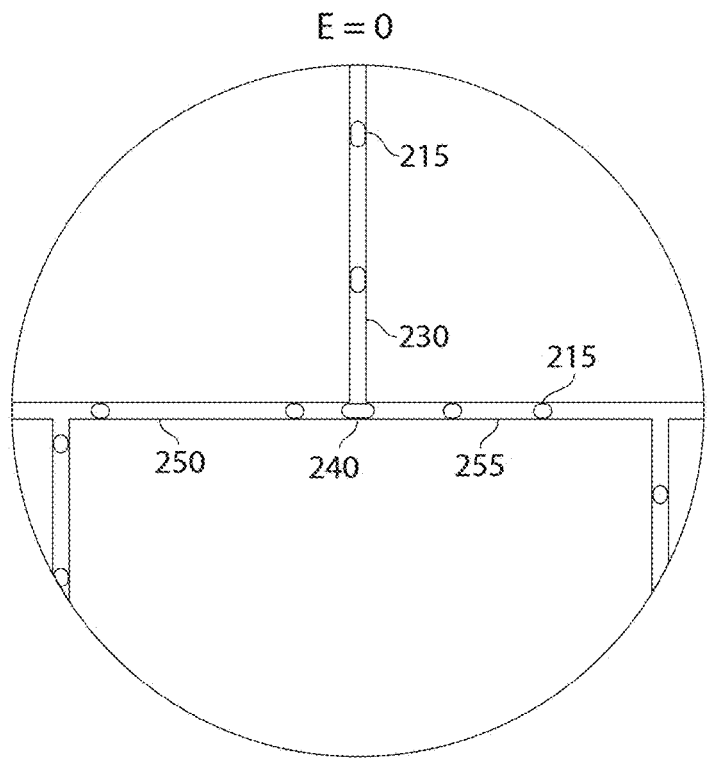
FIGS. 1A and 1B illustrate the splitting of droplets in accordance with one embodiment of the invention.

The present invention generally relates to the control and manipulation of fluidic species, typically surrounded by a liquid (e.g., suspended). Various aspects of the invention relate to forming fluidic droplets, splitting droplets into multiple droplets, creating charges on droplets, inducing dipoles in droplets, causing droplets to fuse or coalesce, causing mixing to occur within droplets, sorting and/or separating droplets, and/or sensing and/or determining droplets and/or components within the droplets. Combinations of these and/or other systems and methods of controlling and manipulating of fluidic species are also envisioned, for example, systems and methods as disclosed in U.S. Provisional Patent Application Ser. No. 60/498,091, filed Aug. 27, 2003, by Link, et. al.; U.S. Provisional Patent Application Ser. No. 60/392,195, filed Jun. 28, 2002, by Stone, et. al.; U.S. Provisional Patent Application Ser. No. 60/424,042, filed Nov. 5, 2002, by Link, et al.; U.S. Pat. No. 5,512,131, issued Apr. 30, 1996 to Kumar, et al.; International Patent Publication WO 96/29629, published Jun. 26, 1996 by Whitesides, et al.; U.S. Pat. No. 6,355,198, issued Mar. 12, 2002 to Kim, et al.; International Patent Application Serial No.: PCT/US01/16973, filed May 25, 2001 by Anderson, et al., published as WO 01/89787 on Nov. 29, 2001;

International Patent Application Ser. No. PCT/US03/20542, filed Jun. 30, 2003 by Stone, et al., published as WO 2004/002627 on Jan. 8, 2004; International Patent Application Ser. No. PCT/US2004/010903, filed Apr. 9, 2004 by Link, et al.; and U.S. Provisional Patent Application Ser. No. 60/461,954, filed Apr. 10, 2003, by Link, et al.; each of which is incorporated herein by reference.

In various aspects of the invention, a fluidic system as disclosed herein may include a droplet formation system, a sensing system, a controller, and/or a droplet sorting and/or separation system, or any combination of these systems. Such systems and methods may be positioned in any suitable order, depending on a particular application, and in some cases, multiple systems of a given type may be used, for example, two or more droplet formation systems, two or more droplet separation systems, etc. As examples of arrangements, systems of the invention can be arranged to form droplets, to dilute fluids, to control the concentration of species within droplets, to sort droplets to select those with a desired concentration of species or entities (e.g., droplets each containing one molecule of reactant), to fuse individual droplets to cause reaction between species contained in the individual droplets, to determine reaction(s) and/or rates of reaction(s) in one or more droplets, etc. Many other arrangements can be practiced in accordance with the invention.

Droplet Production/Formation

One aspect of the invention relates to systems and methods for producing droplets of fluid surrounded by a liquid. The fluid and the liquid may be essentially immiscible in many cases, i.e., immiscible on a time scale of interest (e.g., the time it takes a fluidic droplet to be transported through a particular system or device). In certain cases, the droplets may each be substantially the same shape or size, as further described below.

The fluid may also contain other species, for example, certain molecular species (e.g., as further discussed below), cells, particles, etc.

In one set of embodiments, electric charge may be created on a fluid surrounded by a liquid, which may cause the fluid to separate into individual droplets within the liquid. In some embodiments, the fluid and the liquid may be present in a channel, e.g., a microfluidic channel, or other constricted space that facilitates application of an electric field to the fluid (which may be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc. As one example, in apparatus 5 in FIG. 3A, droplets 15 created by fluid source 10 can be electrically charged using an electric filed created by electric field generator 20.

Electric charge may be created in the fluid within the liquid using any suitable technique, for example, by placing the fluid within an electric field (which may be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. As used herein, a "conductor" is a material having a conductivity of at least about the conductivity of 18 megohm (MOhm or) water. The liquid surrounding the fluid may have a conductivity less than that of the fluid. For instance, the liquid may be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid may be substantially hydrophilic, and the liquid surrounding the fluid may be substantially hydrophobic.

In some embodiments, the charge created on the fluid (for example, on a series of fluidic droplets) may be at least about $10^{-22}$ C/micrometer$^3$. In certain cases, the charge may be at least about $10^{-21}$ C/micrometer$^3$, and in other cases, the charge may be at least about $10^{-20}$ C/micrometer$^3$, at least about $10^{-19}$ C/micrometer$^3$, at least about $10^{-18}$ C/micrometer$^3$, at least about $10^{-17}$ C/micrometer$^3$, at least about $10^{-16}$ C/micrometer$^3$, at least about $10^{-15}$ C/micrometer$^3$, at least about $10^{-14}$ C/micrometer$^3$, at least about $10^{-13}$ C/micrometer$^3$, at least about $10^{-12}$ C/micrometer$^3$, at least about $10^{-11}$ C/micrometer$^3$, at least about $10^{-10}$ C/micrometer$^3$, or at least about $10^{-9}$ C/micrometer$^3$ or more. In certain embodiments, the charge created on the fluid may be at least about $10^{-21}$ C/micrometer$^2$, and in some cases, the charge may be at least about $10^{-20}$ C/micrometer$^2$, at least about $10^{-19}$ C/micrometer$^2$, at least about $10^{-18}$ C/micrometer$^2$, at least about $10^{-17}$ C/micrometer$^2$, at least about $10^{-16}$ C/micrometer$^2$, at least about $10^{-15}$ C/micrometer$^2$, at least about $10^{-14}$ C/micrometer$^2$, or at least about $10^{-13}$ C/micrometer$^2$ or more. In other embodiments, the charge may be at least about $10^{-14}$ C/droplet, and, in some cases, at least about $10^{-13}$ C/droplet, in other cases at least about $10^{-12}$ C/droplet, in other cases at least about $10^{-11}$ C/droplet, in other cases at least about $10^{-10}$ C/droplet, or in still other cases at least about $10^{-9}$ C/droplet.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used. In certain embodiments, the electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

In some embodiments, an electric field may be applied to fluidic droplets to cause the droplets to experience an electric force. The electric force exerted on the fluidic droplets may be, in some cases, at least about 10-16 N/micrometer3. In certain cases, the electric force exerted on the fluidic droplets may be greater, e.g., at least about 10-15 N/micrometer3, at least about 10-14 N/micrometer3, at least about 10-13 N/micrometer3, at least about 10-12 N/micrometer3, at least about 10-11 N/micrometer3, at least about 10-10 N/micrometer3, at least about 10-9 N/micrometer3, at least about 10-8 N/micrometer3, or at least about 10-7 N/micrometer3 or more. In other embodiments, the electric force exerted on the fluidic droplets, relative to the surface area of the fluid, may be at least about 10-15 N/micrometer2, and in some cases, at least about 10-14 N/micrometer2, at least about 10-13 N/micrometer2, at least about 10-12 N/micrometer2, at least about 10-11 N/micrometer2, at least about 10-10 N/micrometer2, at least about 10-9 N/micrometer2, at least about 10-8 N/micrometer2, at least about 10-7 N/micrometer2, or at least about 10-6 N/micrometer2 or more. In yet other embodiments, the electric force exerted on the fluidic droplets may be at least about 10-9 N, at least about 10-8 N, at least about 10-7 N, at least about 10-6 N, at least about 10-5 N, or at least about 10-4 N or more in some cases.

In some embodiments of the invention, systems and methods are provided for at least partially neutralizing an electric charge present on a fluidic droplet, for example, a fluidic droplet having an electric charge, as described above. For example, to at least partially neutralize the electric charge, the fluidic droplet may be passed through an electric field and/or brought near an electrode, e.g., using techniques such as those described herein. Upon exiting of the fluidic droplet from the electric field (i.e., such that the electric field no longer has a strength able to substantially affect the fluidic droplet), and/or other elimination of the electric field, the fluidic droplet may become electrically neutralized, and/or have a reduced electric charge.

Figure 7A:
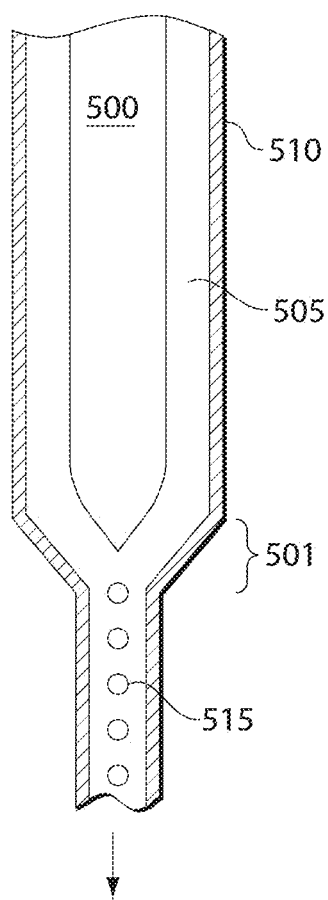
FIGS. 7A and 7B illustrate the formation of droplets in accordance with an embodiment of the invention.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. One example is shown in FIG. 7A, where channel 510 includes a flowing fluid 500 (flowing downwards), surrounded by liquid 505. Channel 510 narrows at location 501, causing fluid 500 to form a series of individual fluidic droplets 515. In other embodiments, internal obstructions may also be used to cause droplet formation to occur. For instance, baffles, ridges, posts, or the like may be used to disrupt liquid flow in a manner that causes the fluid to coalesce into fluidic droplets.

In some cases, the channel dimensions may be altered with respect to time (for example, mechanically or electromechanically, pneumatically, etc.) in such a manner as to cause the formation of individual fluidic droplets to occur. For example, the channel may be mechanically contracted ("squeezed") to cause droplet formation, or a fluid stream may be mechanically disrupted to cause droplet formation, for example, through the use of moving baffles, rotating blades, or the like. As a non-limiting example, in FIG. 7B, fluid 500 flows through channel 510 in a downward direction. Fluid 500 is surrounded by liquid 505. Piezoelectric devices 520 positioned near or integral to channel 510 may then mechanically constrict or "squeeze" channel 510, causing fluid 500 to break up into individual fluidic droplets 515.

In yet another set of embodiments, individual fluidic droplets can be created and maintained in a system comprising three essentially mutually immiscible fluids (i.e., immiscible on a time scale of interest), where one fluid is a liquid carrier, and the second fluid and the third fluid alternate as individual fluidic droplets within the liquid carrier.

Figure 14A:
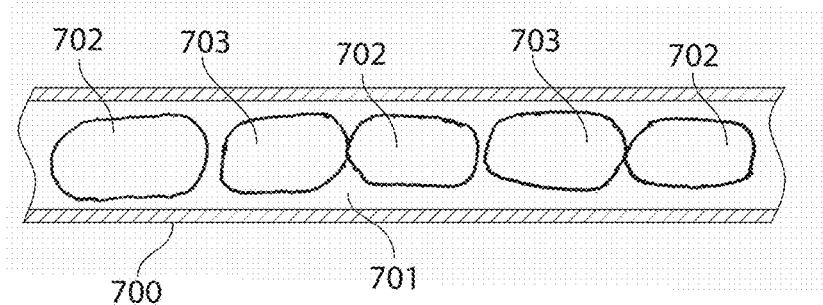
FIGS. 14A-14C illustrate various embodiments of the invention comprising alternating droplets of a first fluid and of a second fluid.

In such a system, surfactants are not necessarily required to ensure separation of the fluidic droplets of the second and third fluids. As an example, with reference to FIG. 14A, within channel 700, a first fluid 701 and a second fluid 702 are each carried within liquid carrier 705. First fluid 701 and second fluid 702 alternate as a series of alternating, individual droplets, each carried by liquid carrier 705 within channel 700.

As the first fluid, the second fluid, and the liquid carrier are all essentially mutually immiscible, any two of the fluids (or all three fluids) can come into contact without causing droplet coalescence to occur. A photomicrograph of an example of such a system is shown in FIG. 14B, illustrating first fluid 701 and second fluid 702, present as individual, alternating droplets, each contained within liquid carrier 705.

Figure 14B:
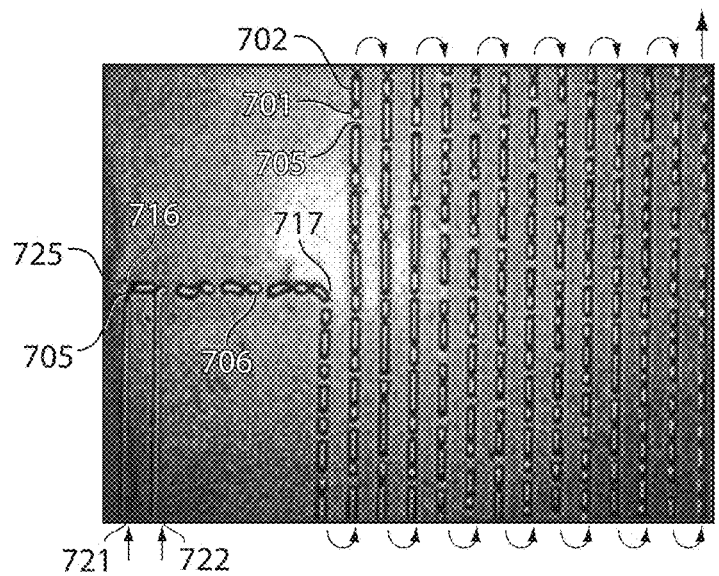

One example of a system involving three essentially mutually immiscible fluids is a silicone oil, a mineral oil, and an aqueous solution (i.e., water, or water containing one or more other species that are dissolved and/or suspended therein, for example, a salt solution, a saline solution, a suspension of water containing particles or cells, or the like). Another example of a system is a silicone oil, a fluorocarbon oil, and an aqueous solution. Yet another example of a system is a hydrocarbon oil (e.g., hexadecane), a fluorocarbon oil, and an aqueous solution. In these examples, any of these fluids may be used as the liquid carrier. Non-limiting examples of suitable fluorocarbon oils include octadecafluorodecahydronaphthalene:

or 1-(1,2,2,3,3,4,4,5,5,6,6-undecafluorocyclohexyl)ethanol:

A non-limiting example of such a system is illustrated in FIG. 14B. In this figure, fluidic network 710 includes a channel containing liquid carrier 705, and first fluid 701 and second fluid 702. Liquid carrier 705 is introduced into fluidic network 710 through inlet 725, while first fluid 701 is introduced through inlet 721, and second fluid 702 is introduced through inlet 722. Channel 716 within fluidic network 710 contains liquid carrier 715 introduced from inlet 725. Initially, first fluid 701 is introduced into liquid carrier 705, forming fluidic droplets therein. Next, second fluid 702 is introduced into liquid 705, forming fluidic droplets therein that are interspersed with the fluidic droplets containing first fluid 701. Thus, upon reaching channel 717, liquid carrier 705 contains a first set of fluidic droplets containing first fluid 701, interspersed with a second set of fluidic droplets containing second fluid 702. In the embodiment illustrated, channel 706 optionally comprises a series of bends, which may allow mixing to occur within each of the fluidic droplets, as further discussed below. However, it should be noted that in this embodiment, since first fluid 701 and second fluid 702 are essentially immiscible, significant fusion and/or mixing of the droplets containing first fluid 701 with the droplets containing second fluid 702 is not generally expected.

Other examples of the production of droplets of fluid surrounded by a liquid are described in International Patent Application Ser. No. PCT/US2004/010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference.

In some embodiments, the fluidic droplets may each be substantially the same shape and/or size. The shape and/or size can be determined, for example, by measuring the average diameter or other characteristic dimension of the droplets. The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasi-electric light scattering; polarimetry; refractometry; or turbidity measurements.

The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases. In certain embodiments of the invention, the fluidic droplets may contain additional entities, for example, other chemical, biochemical, or biological entities (e.g., dissolved or suspended in the fluid), cells, particles, gases, molecules, or the like. In some cases, the droplets may each be substantially the same shape or size, as discussed above. In certain instances, the invention provides for the production of droplets consisting essentially of a substantially uniform number of entities of a species therein (i.e., molecules, cells, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases. In one set of embodiments, in a liquid containing droplets of fluid, some of which contain a species of interest and some of which do not contain the species of interest, the droplets of fluid may be screened or sorted for those droplets of fluid containing the species as further described below (e.g., using fluorescence or other techniques such as those described above), and in some cases, the droplets may be screened or sorted for those droplets of fluid containing a particular number or range of entities of the species of interest, e.g., as previously described. Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 750, at least about 1000, at least about 2000, or at least about 5000 or more in some cases. In other cases, the enrichment (or depletion) may be in a ratio of at least about 104, at least about 105, at least about 106, at least about 107, at least about 108, at least about 109, at least about 1010, at least about 1011, at least about 1012, at least about 1013, at least about 1014, at least about 1015, or more. For example, a fluidic droplet containing a particular species may be selected from a library of fluidic droplets containing various species, where the library may have about 105, about 106, about 107, about 108, about 109, about 1010, about 1011, about 1012, about 1013, about 1014, about 1015, or more items, for example, a DNA library, an RNA library, a protein library, a combinatorial chemistry library, etc. In certain embodiments, the droplets carrying the species may then be fused, reacted, or otherwise used or processed, etc., as further described below, for example, to initiate or determine a reaction.

Splitting Droplets

In another aspect, the invention relates to systems and methods for splitting a fluidic droplet into two or more droplets. The fluidic droplet may be surrounded by a liquid, e.g., as previously described, and the fluid and the liquid are essentially immiscible in some cases. The two or more droplets created by splitting the original fluidic droplet may each be substantially the same shape and/or size, or the two or more droplets may have different shapes and/or sizes, depending on the conditions used to split the original fluidic droplet. In many cases, the conditions used to split the original fluidic droplet can be controlled in some fashion, for example, manually or automatically (e.g., with a processor, as discussed below). In some cases, each droplet in a plurality or series of fluidic droplets may be independently controlled. For example, some droplets may be split into equal parts or unequal parts, while other droplets are not split.

According to one set of embodiments, a fluidic droplet can be split using an applied electric field. The electric field may be an AC field, a DC field, etc. The fluidic droplet, in this embodiment, may have a greater electrical conductivity than the surrounding liquid, and, in some cases, the fluidic droplet may be neutrally charged. In some embodiments, the droplets produced from the original fluidic droplet are of approximately equal shape and/or size. In certain embodiments, in an applied electric field, electric charge may be urged to migrate from the interior of the fluidic droplet to the surface to be distributed thereon, which may thereby cancel the electric field experienced in the interior of the droplet. In some embodiments, the electric charge on the surface of the fluidic droplet may also experience a force due to the applied electric field, which causes charges having opposite polarities to migrate in opposite directions. The charge migration may, in some cases, cause the drop to be pulled apart into two separate fluidic droplets. The electric field applied to the fluidic droplets may be created, for example, using the techniques described above, such as with a reaction an electric field generator, etc.

Figure 1B:
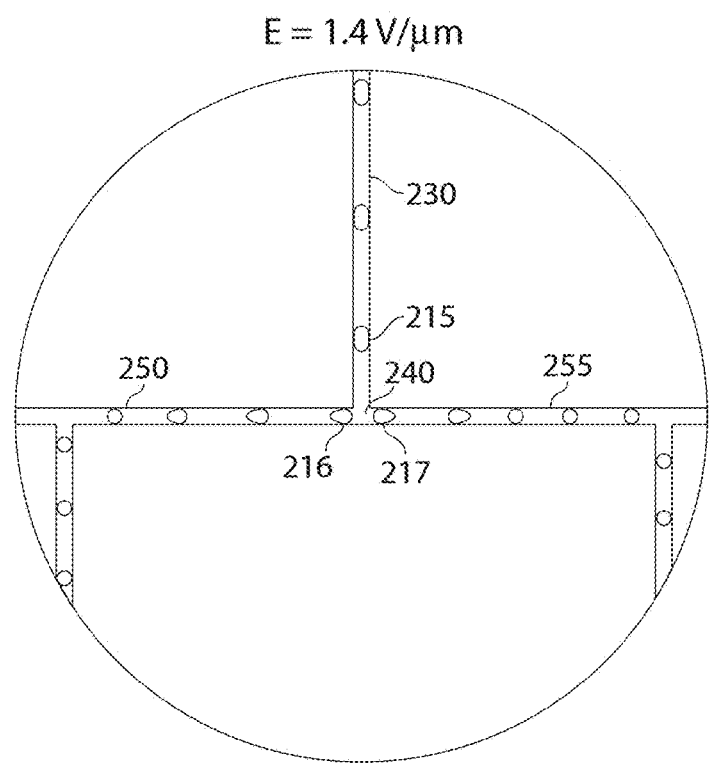

As a non-limiting example, in FIG. 1A, where no electric field is applied, fluidic droplets 215 contained in channel 230 are carried by a surrounding liquid, which flows towards intersection 240, leading to channels 250 and 255. In this example, the surrounding liquid flows through channels 250 and 255 at equal flowrates. Thus, at intersection 240, fluidic droplets 215 do not have a preferred orientation or direction, and move into exit channels 250 and 255 with equal probability due to the surrounding liquid flow. In contrast, in FIG. 1B, while the surrounding liquid flows in the same fashion as FIG. 1A, under the influence of an applied electric field of 1.4 V/micrometers, fluidic droplets 215 are split into two droplets at intersection 240, forming new droplets 216 and 217. Droplet 216 moves to the left in channel 250, while droplet 217 moves to the right in channel 255.

Figure 5:
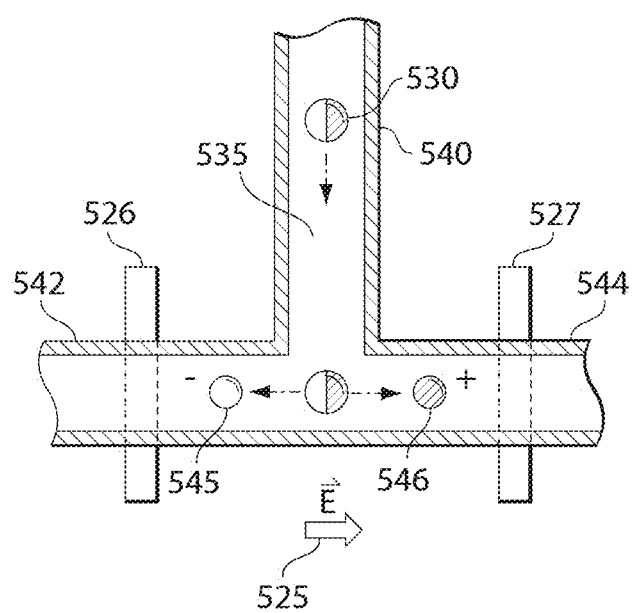
FIG. 5 is a schematic diagram of droplet splitting, in accordance with one embodiment of the invention.

A schematic of this process can be seen in FIG. 5, where a neutral fluidic droplet 530, surrounded by a liquid 535 in channel 540, is subjected to applied electric field 525, created by electrodes 526 and 527. Electrode 526 is positioned near channel 542, while electrode 527 is positioned near channel 544. Under the influence of electric field 525, charge separation is induced within fluidic droplet 530, i.e., such that a positive charge is induced at one end of the droplet, while a negative charge is induced at the other end of the droplet. The droplet may then split into a negatively charged droplet 545 and a positively charged droplet 546, which then may travel in channels 542 and 544, respectively. In some cases, one or both of the electric charges on the resulting charged droplets may also be neutralized, as previously described.

Other examples of splitting a fluidic droplet into two droplets are described in International Patent Application Serial No. PCT/US2004/010903, filed Apr. 9, 2004 by Link, et al.; U.S. Provisional Patent Application Serial No. 60/498, 091, filed Aug. 27, 2003, by Link, et. al.; and International Patent Application Serial No. PCT/US03/20542, filed Jun. 30, 2003 by Stone, et al., published as WO 2004/002627 on Jan. 8, 2004, each incorporated herein by reference.

Fusing Droplets

The invention, in yet another aspect, relates to systems and methods for fusing or coalescing two or more fluidic droplets into one droplet. For example, in one set of embodiments, systems and methods are provided that are able to cause two or more droplets (e.g., arising from discontinuous streams of fluid) to fuse or coalesce into one droplet in cases where the two or more droplets ordinarily are unable to fuse or coalesce, for example, due to composition, surface tension, droplet size, the presence or absence of surfactants, etc. In certain microfluidic systems, the surface tension of the droplets, relative to the size of the droplets, may also prevent fusion or coalescence of the droplets from occurring in some cases.

Figure 13A:
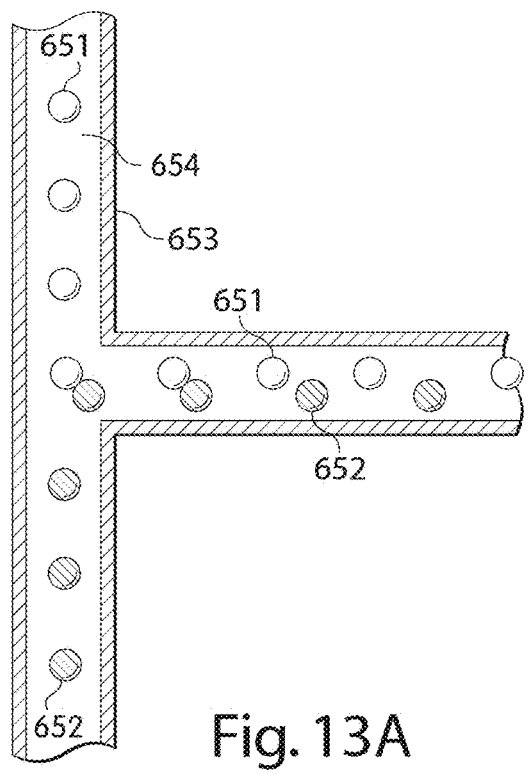
Figure 13B:
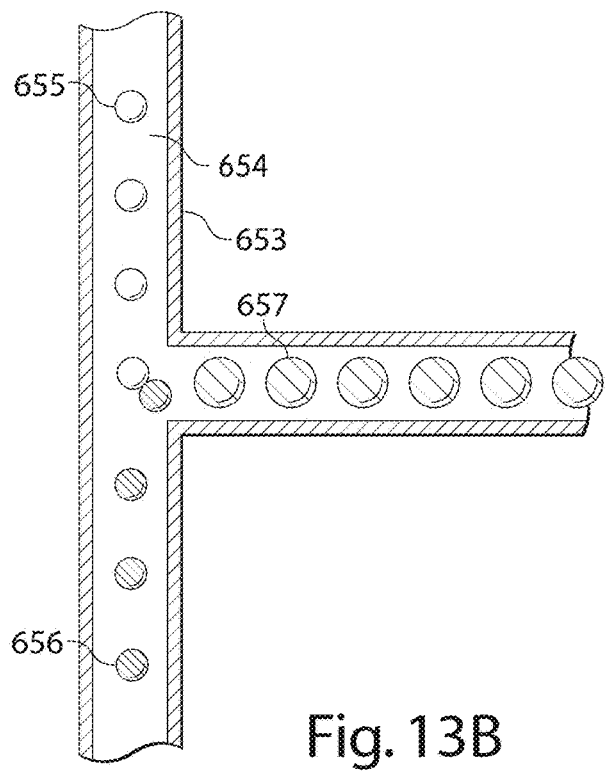

In one embodiment, two fluidic droplets may be given opposite electric charges (i.e., positive and negative charges, not necessarily of the same magnitude), which may increase the electrical interaction of the two droplets such that fusion or coalescence of the droplets can occur due to their opposite electric charges, e.g., using the techniques described herein. For instance, an electric field may be applied to the droplets, the droplets may be passed through a capacitor, a chemical reaction may cause the droplets to become charged, etc. As an example, as is shown schematically in FIG. 13A, uncharged droplets 651 and 652, carried by a liquid 654 contained within a microfluidic channel 653, are brought into contact with each other, but the droplets are not able to fuse or coalesce, for instance, due to their size and/or surface tension. The droplets, in some cases, may not be able to fuse even if a surfactant is applied to lower the surface tension of the droplets. However, if the fluidic droplets are electrically charged with opposite charges (which can be, but are not necessarily of, the same magnitude), the droplets may be able to fuse or coalesce. For instance, in FIG. 13B, positively charged droplets 655 and negatively charged droplets 656 are directed generally towards each other such that the electrical interaction of the oppositely charged droplets causes the droplets to fuse into fused droplets 657.

In another embodiment, the fluidic droplets may not necessarily be given opposite electric charges (and, in some cases, may not be given any electric charge), and are fused through the use of dipoles induced in the fluidic droplets that causes the fluidic droplets to coalesce. In the example illustrated in FIG. 13C, droplets 660 and 661 (which may each independently be electrically charged or neutral), surrounded by liquid 665 in channel 670, move through the channel such that they are the affected by an applied electric field 675. Electric field 675 may be an AC field, a DC field, etc., and may be created, for instance, using electrodes 676 and 677, as shown here. The induced dipoles in each of the fluidic droplets, as shown in FIG. 13C, may cause the fluidic droplets to become electrically attracted towards each other due to their local opposite charges, thus causing droplets 660 and 661 to fuse to produce droplet 663. In FIG. 13D, droplets 660 and 661.

Figure 12A:
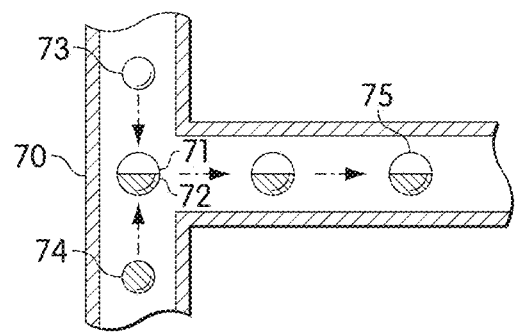
FIGS. 12A-12J illustrate fluidic mixing in droplets having two or more fluid regions, according to one embodiment of the invention.
Figure 12B:
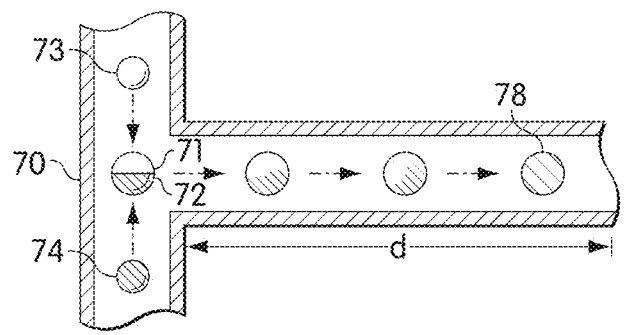
Figure 12C:
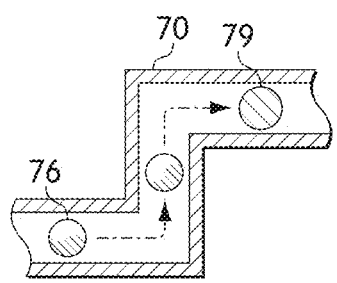
Figure 12D:
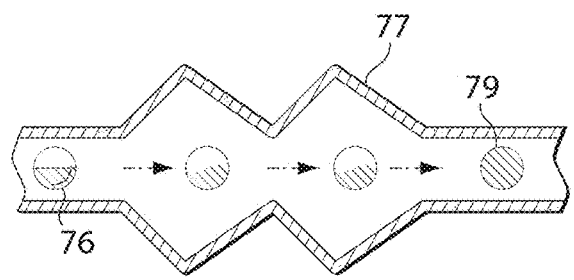
Figure 12E:
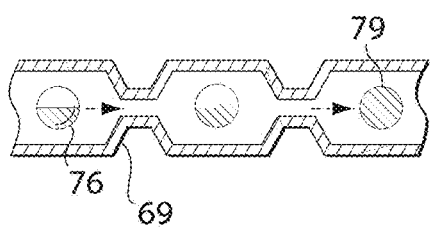
Figure 12F:
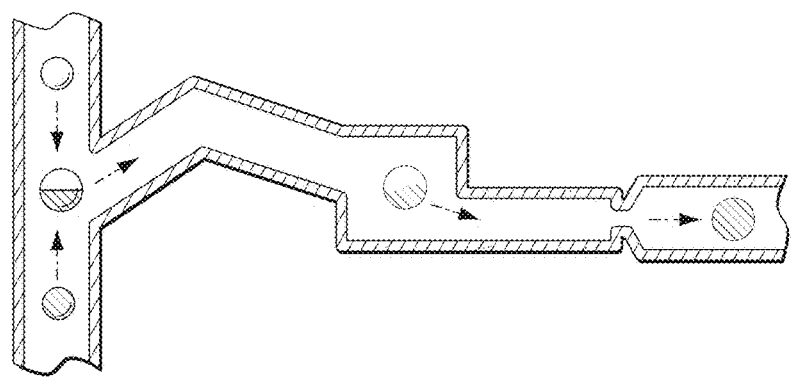
Figure 12G:
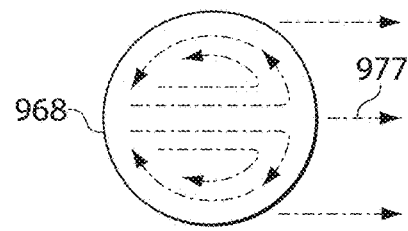
Figure 12H:
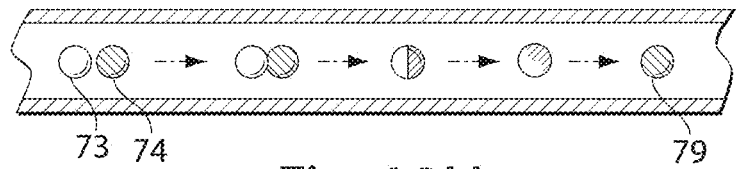
Figure 12I:
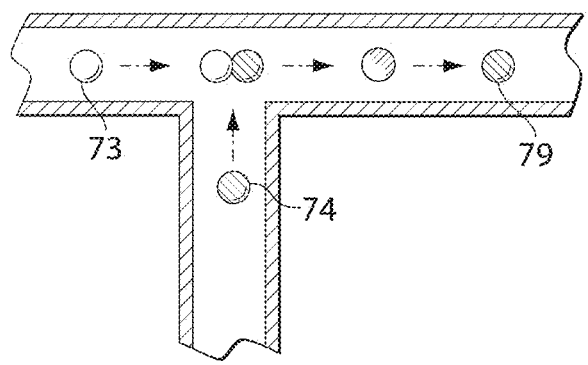
Figure 12J:
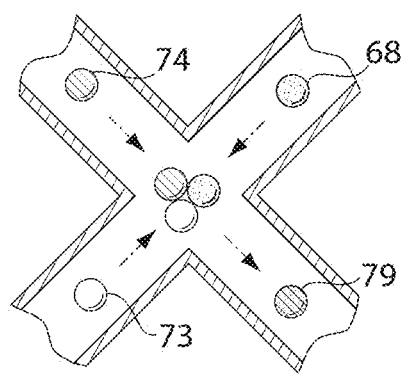

It should be noted that, in various embodiments, the two or more droplets allowed to coalesce are not necessarily required to meet "head-on." Any angle of contact, so long as at least some fusion of the droplets initially occurs, is sufficient. As an example, in FIG. 12H, droplets 73 and 74 each are traveling in substantially the same direction (e.g., at different velocities), and are able to meet and fuse. As another example, in FIG. 12I, droplets 73 and 74 meet at an angle and fuse. In FIG. 12J, three fluidic droplets 73, 74 and 68 meet and fuse to produce droplet 79. Other examples of fusing or coalescing fluidic droplets are described in International Patent Application Serial No. PCT/US2004/ 010903, filed Apr. 9, 2004 by Link, et al., incorporated herein by reference.

Mixing within Droplets

In a related aspect, the invention relates to systems and methods for allowing the mixing of more than one fluid to occur within a fluidic droplet. For example, in various embodiments of the invention, two or more fluidic droplets may be allowed to fuse or coalesce, as described above, and then, within the fused droplet, the two or more fluids from the two or more original fluidic droplets may then be allowed to mix. It should be noted that when two droplets fuse or coalesce, perfect mixing within the droplet does not instantaneously occur. Instead, for example, as is shown in FIG. 12B, the coalesced droplet may initially be formed of a first fluid region 71 (from first droplet 73) and a second fluid region 72 (from second droplet 74). Thus, in some cases, the fluid regions may remain as separate regions, for example, due to internal "counter-revolutionary" flow within the fluidic droplet (shown in FIG. 12G with droplet 968, direction indicated by arrow 977), thus resulting in a non-uniform fluidic droplet 75, as is shown in FIG. 12A.

Figure 7B:
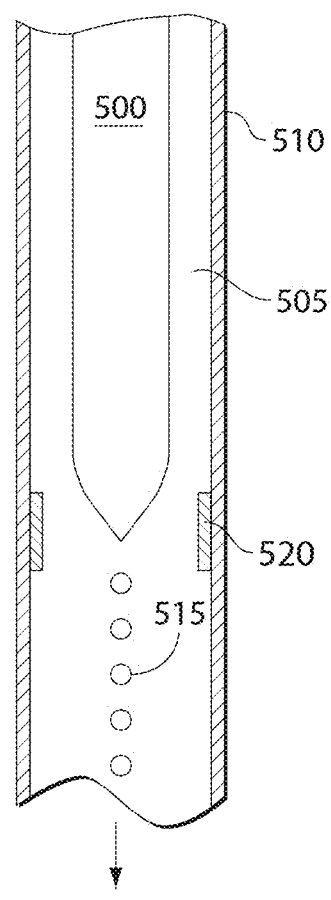

However, in other cases, the fluid regions within the fluidic droplet may be allowed to mix, react, or otherwise interact with each other, as is shown in FIG. 7B, resulting in mixed or partially mixed fluidic droplet 78. The mixing may occur through natural means, for example, through diffusion (e.g., through the interface between the regions), through reaction of the fluids with each other, through fluid flow within the droplet (i.e., convection), etc. However, in some cases, mixing of the regions 71 and 72 may be enhanced through certain systems external of the fluidic droplet. For example, the fluidic droplet may be passed through one or more channels or other systems which cause the droplet to change its velocity and/or direction of movement. The change of direction may alter convection patterns within the droplet, causing the fluids to be at least partially mixed. As an example, in FIG. 12C, droplet 76 may be passed through one or more bends within a channel, causing the fluids within droplet 76 to be at least partially mixed, resulting in droplet 79; or droplet 76 may pass by one or more obstructions within the channel, etc. As another example, in FIG. 12D, droplet 76 passes through one or more expansion regions 77 within a channel, causing the fluids within droplet 76 to be at least partially mixed, resulting in droplet 79. In FIG. 12E, droplet 76 passes through one or more constriction regions 69, causing the fluids within droplet 76 to be at least partially mixed, resulting in droplet 79. Combinations are also possible. For example, in FIG. 12F, droplet 76 passes through bend 70, expansion region 77, and constriction region 69, causing at least partial mixing of the fluid regions within the droplet to occur. As yet another example, channel 706 in FIG. 14B contains a series of bends, which may allow mixing of the fluids within the droplets within channel 706 to occur.

Figure 14C:
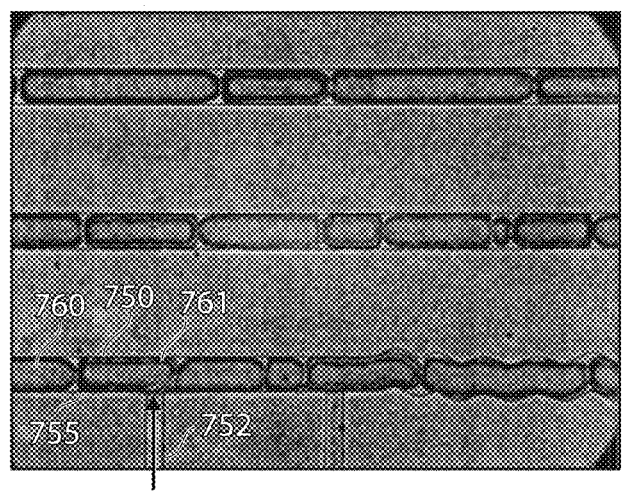

In one set of embodiments, a fluid may be injected into a fluidic droplet, which may cause mixing of the injected fluid with the other fluids within the fluidic droplet to occur. The fluid may be microinjected into the fluidic droplet in some cases, e.g., using a microneedle or other such device. In other cases, the fluid may be injected directly into a fluidic droplet using a fluidic channel as the fluidic droplet comes into contact with the fluidic channel. For instance, referring now to FIG. 14C, channel 750 contains a carrier fluid 755 containing a series of fluidic droplets 760. Droplet 761 is in contact with fluidic channel 752. A fluid can then be introduced into fluidic droplet 761 through fluidic channel 752, which fluid may be the same or different than the fluid in fluidic droplet 761.

Other examples of fluidic mixing in droplets are described in International Patent Application Serial No. PCT/US2004/010903, filed Apr. 9, 2004 by Link, et al., incorporated herein by reference.

Screening/Sorting Droplets

In still another aspect, the invention provides systems and methods for screening or sorting fluidic droplets in a liquid, and in some cases, at relatively high rates. For example, a characteristic of a droplet may be sensed and/or determined in some fashion (e.g., as further described below), then the droplet may be directed towards a particular region of the device, for example, for sorting or screening purposes.

In some embodiments, a characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In some cases, high sorting speeds may be achievable using certain systems and methods of the invention. For instance, at least about 10 droplets per second may be determined and/or sorted in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted in such a fashion.

Figure 2A:
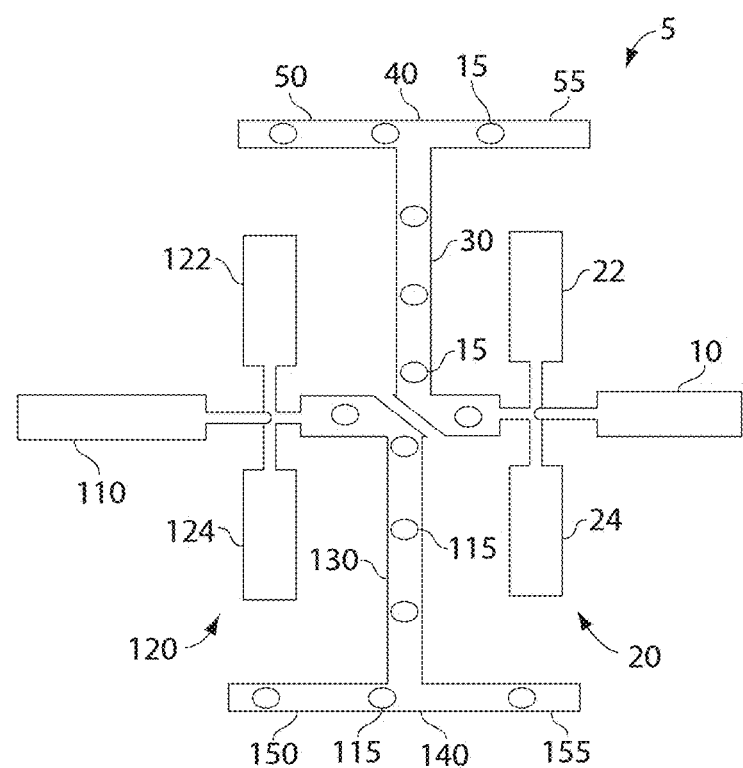
FIGS. 2A and 2B illustrate an apparatus in accordance with an embodiment of the invention, before the application of an electric field thereto.
Figure 4A:
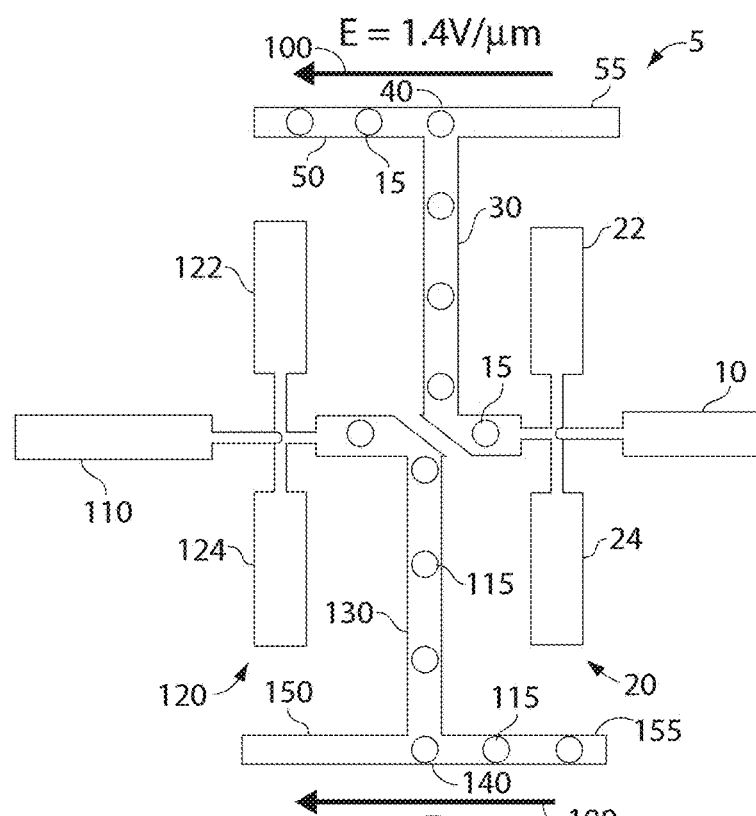
FIGS. 4A and 4B illustrate the apparatus of FIGS. 2A and 2B after the application of a reversed electric field thereto.

In one set of embodiments, a fluidic droplet may be directed by creating an electric charge (e.g., as previously described) on the droplet, and steering the droplet using an applied electric field, which may be an AC field, a DC field, etc. As an example, in reference to FIGS. 2-4, an electric field may be selectively applied and removed (or a different electric field may be applied, e.g., a reversed electric field as shown in FIG. 4A) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system. As a particular example, in FIGS. 2A, 3A and 4A, a liquid containing fluidic droplets 15 flows from fluid source 10, through channel 30 to intersection 40, and exits through channels 50 and 55. In FIG. 2A, fluidic droplets 15 are directed through both channels 50 and 55, while in FIG. 3A, fluidic droplets 15 are directed to only channel 55 and, in FIG. 4A, fluidic droplets 15 are directed to only channel 50. In another set of embodiments, a fluidic droplet may be sorted or steered by inducing a dipole in the fluidic droplet (which may be initially charged or uncharged), and sorting or steering the droplet using an applied electric field. The electric field may be an AC field, a DC field, etc. For example, with reference to FIG. 9A, a channel 540, containing fluidic droplet 530 and liquid 535, divides into channel 542 and 544. Fluidic droplet 530 may have an electric charge, or it may be uncharged. Electrode 526 is positioned near channel 542, while electrode 527 is positioned near channel 544. Electrode 528 is positioned near the junction of channels 540, 542, and 544. In FIGS. 9C and 9D, a dipole is induced in the fluidic droplet using electrodes 526, 527, and/or 528. In FIG. 9C, a dipole is induced in droplet 530 by applying an electric field 525 to the droplet using electrodes 527 and 528. Due to the strength of the electric field, the droplet is strongly attracted to the right, into channel 544. Similarly, in FIG. 9D, a dipole is induced in droplet 530 by applying an electric field 525 to the droplet using electrodes 526 and 528, causing the droplet to be attracted into channel 542. Thus, by applying the proper electric field, droplet 530 can be directed to either channel 542 or 544 as desired. In other embodiments, however, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. As a non-limiting example, with reference to FIG. 10A, fluidic droplet 570 is surrounded by a liquid 575 in channel 580. Channel 580 divides into three channels 581, 582, and 583. The flow of liquid 575 can be directed into any of channels 581, 582, and 583 as desired, for example, using flow-controlling devices known to those of ordinary skill in the art, for example, valves, pumps, pistons, etc. Thus, in FIG. 10B, fluidic droplet 570 is directed into channel 581 by directing liquid 575 to flow into channel 581 (indicated by arrows 574); in FIG. 10C, fluidic droplet 570 is directed into channel 582 by directing liquid 575 to flow into channel 582 (indicated by arrows 574); and in FIG. 10D, fluidic droplet 570 is directed into channel 583 by directing liquid 575 to flow into channel 583 (indicated by arrows 574).

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal.

Figure 11A:
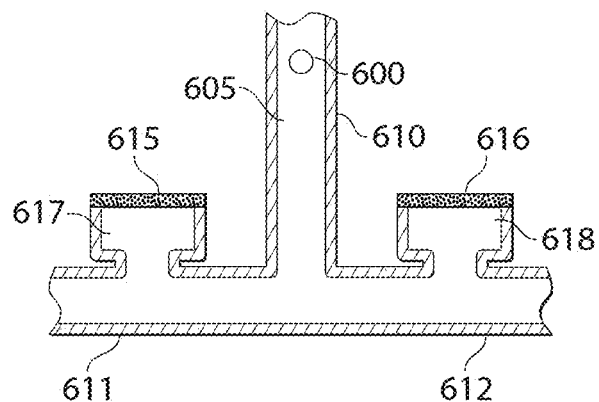
FIGS. 11A-11C illustrate the sorting of fluidic droplets according to yet another embodiment of the invention.
Figure 11B:
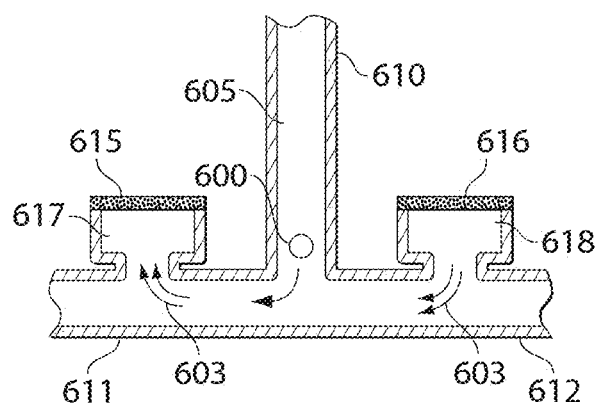
Figure 11C:
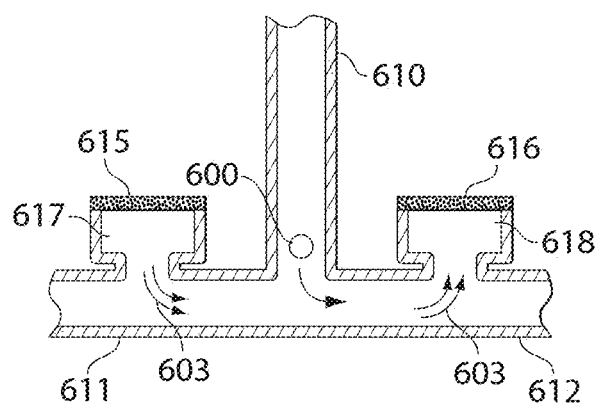

As a non-limiting example, in FIG. 11A, fluidic droplet 600 is surrounded by a liquid 605 in channel 610. Channel 610 divides into channels 611, 612. Positioned in fluidic communication with channels 611 and 612 are liquid reservoirs 617 and 618, which may be expanded and/or contracted, for instance, by piezoelectric components 615 and 616, by a piston (not shown), etc. In FIG. 11B, liquid reservoir 617 has been expanded, while liquid reservoir 618 has been contracted. The effect of the expansion/contractions of the reservoirs is to cause a net flow of liquid towards channel 611, as indicated by arrows 603. Thus, fluidic droplet 600, upon reaching the junction between the channels, is directed to channel 611 by the movement of liquid 605. The reverse situation is shown in FIG. 11C, where liquid reservoir 617 has contracted while liquid reservoir 618 has been expanded. A net flow of liquid occurs towards channel 612 (indicated by arrows 603), causing fluidic droplet 600 to move into channel 612. It should be noted, however, that reservoirs 617 and 618 do not both need to be activated to direct fluidic droplet 600 into channels 611 or 612. For example, in one embodiment, fluidic droplet 600 may be directed to channel 611 by the expansion of liquid reservoir 617 (without any alteration of reservoir 618), while in another embodiment, fluidic droplet 600 may be directed to channel 611 by the contraction of liquid reservoir 618 (without any alteration of reservoir 617). In some cases, more than two liquid reservoirs may be used.

Figure 6A:
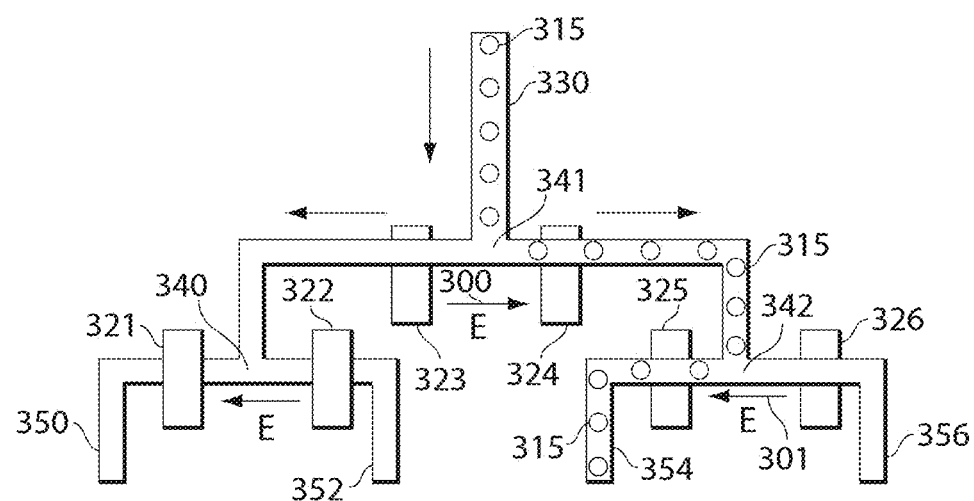
FIGS. 6A and 6B are schematic diagrams of additional embodiments of the invention.
Figure 6B:
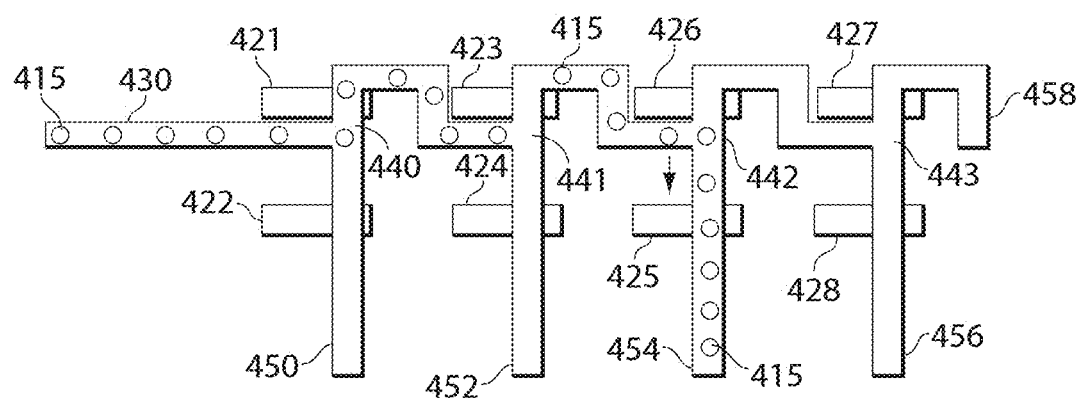

In some embodiments, the fluidic droplets may be sorted into more than two channels. Non-limiting examples of embodiments of the invention having multiple regions within a fluidic system for the delivery of droplets are shown in FIGS. 6A and 6B. Other arrangements are shown in FIGS. 10A-10D. In FIG. 6A, charged droplets 315 in channel 330 may be directed as desired to any one of exit channels 350, 352, 354, or 356, by applying electric fields to control the movement of the droplets at intersections 340, 341, and 342, using electrodes 321/322, 323/324, and 325/326, respectively. In FIG. 6A, droplets 315 are directed to channel 354 using applied electric fields 300 and 301, using principles similar to those discussed above. Similarly, in FIG. 6B, charged droplets 415 in channel 430 can be directed to any one of exit channels 450, 452, 454, 456, or 458, by applying electric fields to control the movement of the droplets at intersections 440, 441, 442, and 443, using electrodes 421/422, 423/424, 425/426, and 427/428, respectively. In this figure, droplets 415 are directed to channel 454; of course, the charged droplets may be directed to any other exit channel as desired.

Figure 2B:
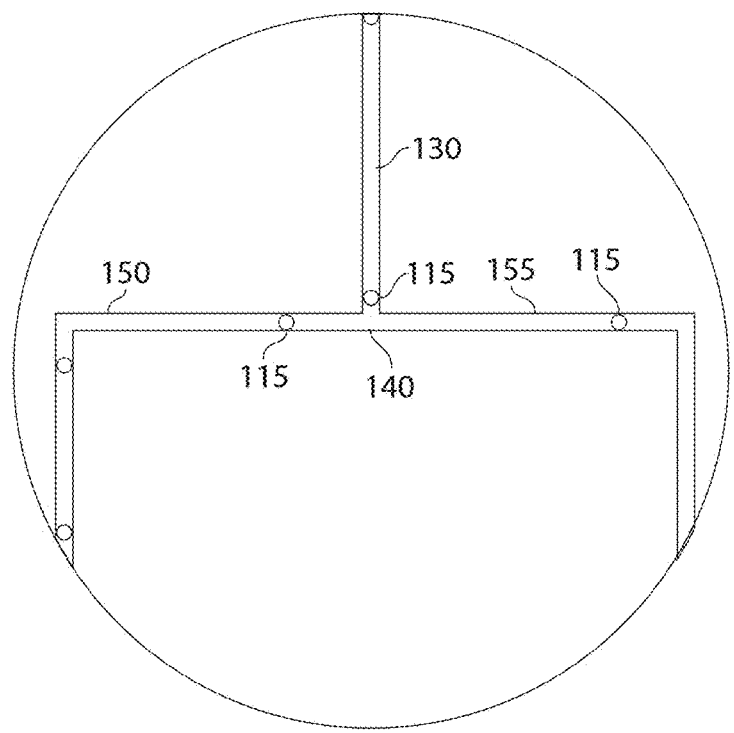

In another example, in apparatus 5, as schematically illustrated in FIG. 2A, fluidic droplets 15 created by fluid source 10 are positively charged due to an applied electric field created using electric field generator 20, which comprises two electrodes 22, 24. Fluidic droplets 15 are directed through channel 30 by a liquid containing the droplets, and are directed towards intersection 40. At intersection 40, the fluidic droplets do not have a preferred orientation or direction, and move into exit channels 50 and 55 with equal probability (in this embodiment, liquid drains through both exit channels 50 and 55 at substantially equal rates). Similarly, fluidic droplets 115 created by fluid source 110 are negatively charged due to an applied electric field created using electric field generator 120, which comprises electrodes 122 and 124. After traveling through channel 130 towards intersection 140, the fluidic droplets do not have a preferred orientation or direction, and move into exit channels 150 and 155 with equal probability, as the liquid exits through exit channels 150 and 155 at substantially equal rates. A representative photomicrograph of intersection 140 is shown in FIG. 2B.

In the schematic diagram of FIG. 3A, an electric field 100 of 1.4 V/micrometer has been applied to apparatus 5 of FIG. 2A, in a direction towards the right of apparatus 5. Positively-charged fluidic droplets 15 in channel 30, upon reaching intersection 40, are directed to the right in channel 55 due to the applied electric field 100, while the liquid containing the droplets continues to exit through exit channels 50 and 55 at substantially equal rates. Similarly, negatively-charged fluidic droplets 115 in channel 130, upon reaching intersection 140, are directed to the left in channel 150 due to the applied electric field 100, while the liquid fluid continues to exit the device through exit channels 150 and 155 at substantially equal rates. Thus, electric field 100 can be used to direct fluidic droplets into particular channels as desired. A representative photomicrograph of intersection 140 is shown in FIG. 3B.

Figure 4B:
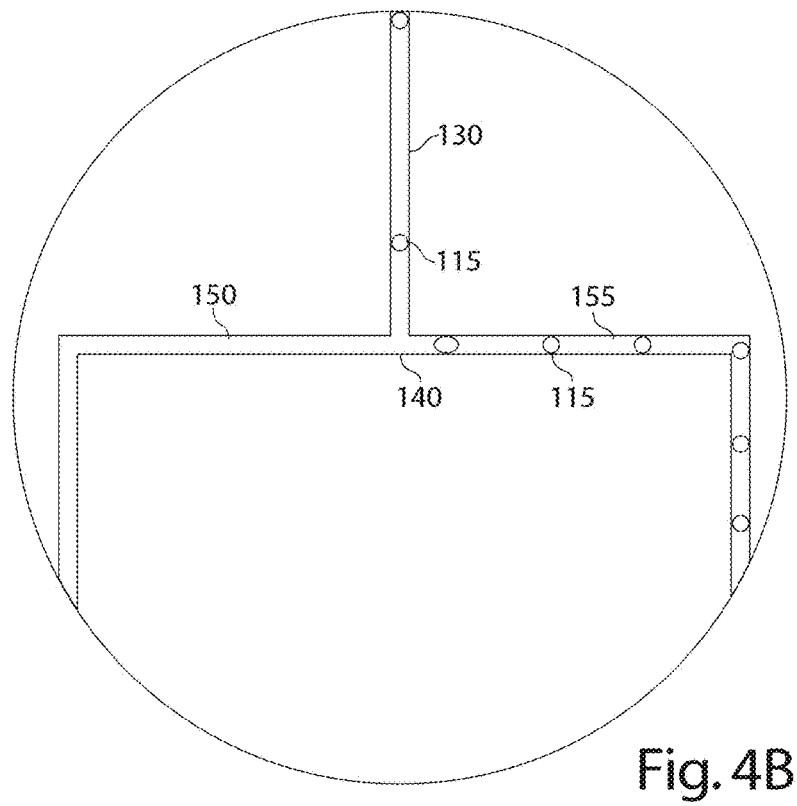

FIG. 4A is a schematic diagram of apparatus 5 of FIG. 2A, also with an applied electric field 100 of 1.4 V/micrometer, but in the opposite direction (i.e., −1.4 V/micrometer). In this figure, positively-charged fluidic droplets 15 in channel 30, upon reaching intersection 40, are directed to the left into channel 50 due to the applied electric field 100, while negatively-charged fluidic droplets 115 in channel 130, upon reaching intersection 140, are directed to the right into channel 155 due to applied electric field 100. The liquid containing the droplets exits through exit channels 50 and 55, and 150 and 155, at substantially equal rates. A representative photomicrograph of intersection 140 is shown in FIG. 4B.

In some embodiments of the invention, a fluidic droplet may be sorted and/or split into two or more separate droplets, for example, depending on the particular application. Any of the above-described techniques may be used to split and/or sort droplets. As a non-limiting example, by applying (or removing) a first electric field to a device (or a portion thereof), a fluidic droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc. In a series of droplets, each droplet may be independently sorted and/or split; for example, some droplets may be directed to one location or another, while other droplets may be split into multiple droplets directed to two or more locations.

Figure 8A:
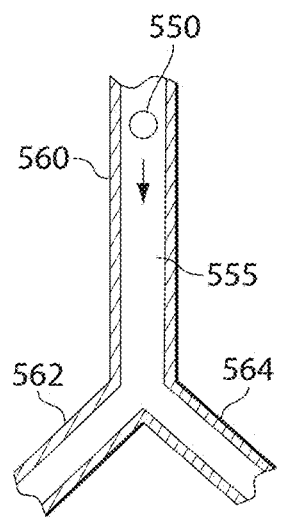
FIGS. 8A-8F illustrate the sorting and/or splitting of droplets in accordance with one embodiment of the invention.
Figure 8B:
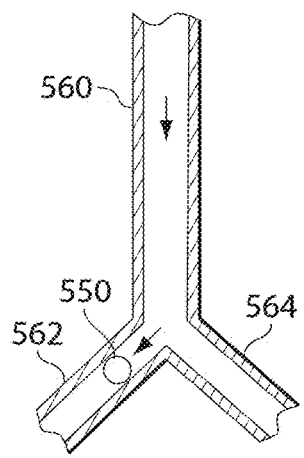
Figure 8C:
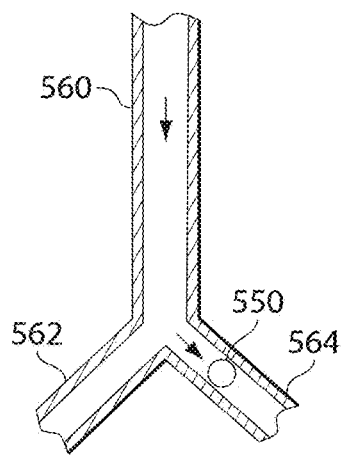
Figure 8D:
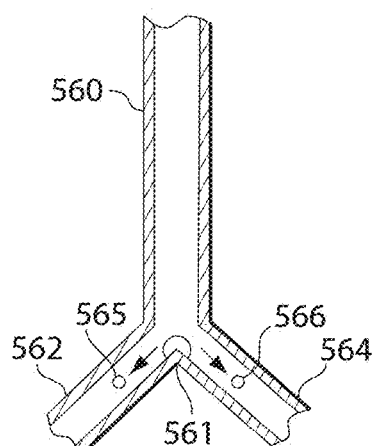
Figure 8E:
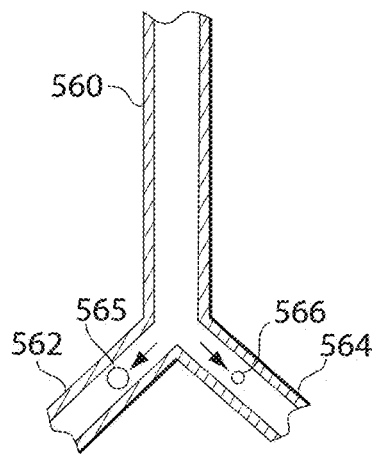
Figure 8F:
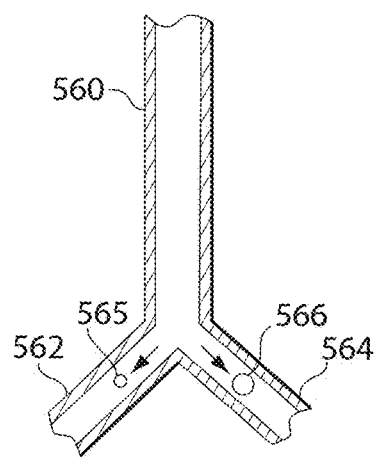

As one particular example, in FIG. 8A, fluidic droplet 550, surrounding liquid 555 in channel 560 may be directed to channel 556, channel 557, or be split in some fashion between channels 562 and 564. In FIG. 8B, by directing surrounding liquid 555 towards channel 562, fluidic droplet 550 may be directed towards the left into channel 562; in FIG. 8C, by directing surrounding liquid 555 towards channel 564, fluidic droplet 550 may be directed towards the right into channel 564, In FIG. 8D, an electric field may be applied, in combination with control of the flow of liquid 555 surrounding fluidic droplet 550, that causes the droplet to impact junction 561, which may cause the droplet to split into two separate fluidic droplets 565, 566. Fluidic droplet 565 is directed to channel 562, while fluidic droplet 566 is directed to channel 566. A high degree of control of the applied electric field may be achieved to control droplet formation; thus, for example, after fluidic droplet 565 has been split into droplets 565 and 566, droplets 565 and 566 may be of substantially equal size, or either of droplets 565 and 566 may be larger, e.g., as is shown in FIGS. 8E and 8F, respectively.

Figure 9A:
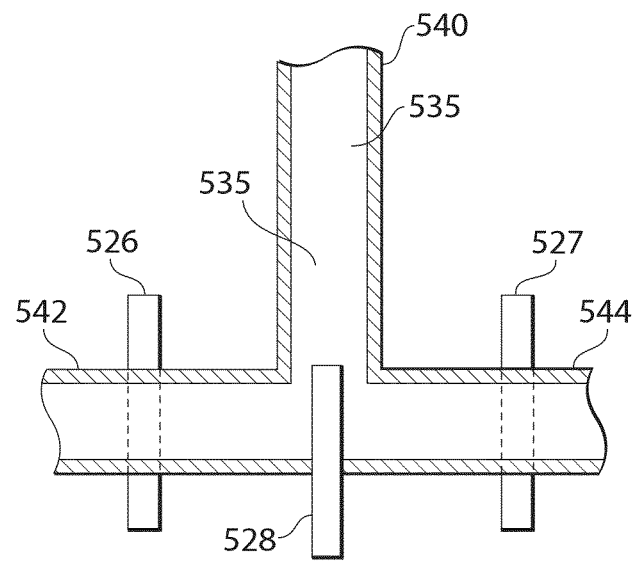
FIGS. 9A-9D illustrate the sorting and/or splitting of droplets in accordance with another embodiment of the invention.
Figure 9B:
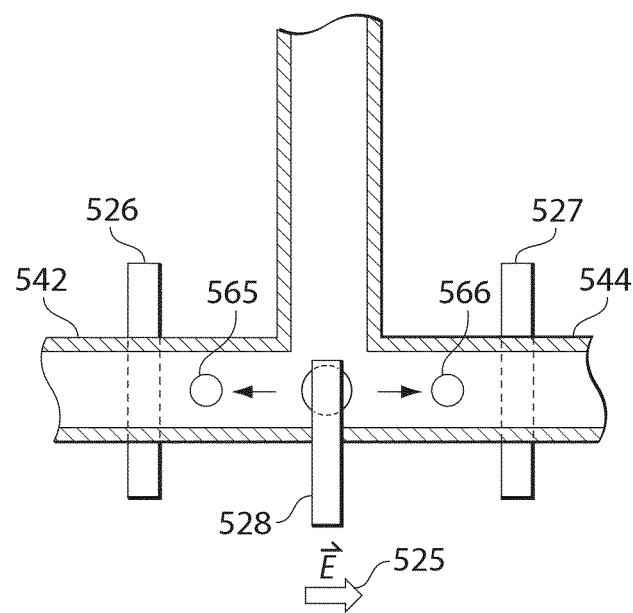
Figure 9C:
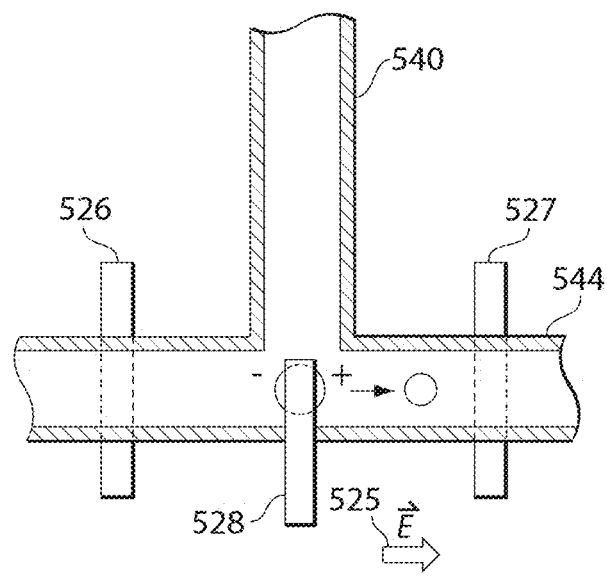
Figure 9D:
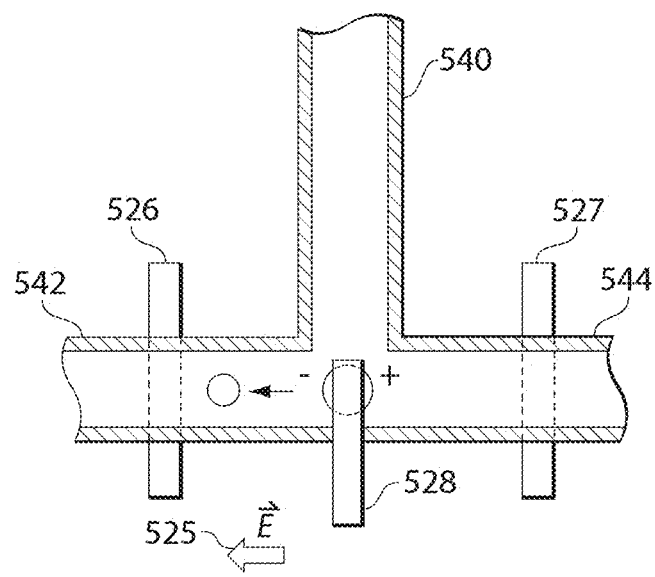
Figure 10A:
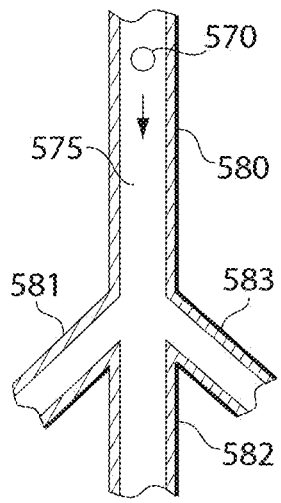
FIGS. 10A-10D illustrate the sorting of fluidic droplets according to another embodiment of the invention.
Figure 10B:
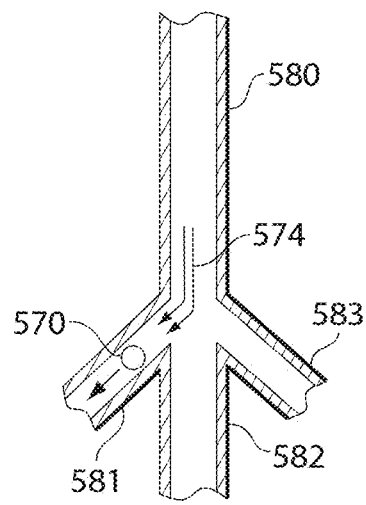
Figure 10C:
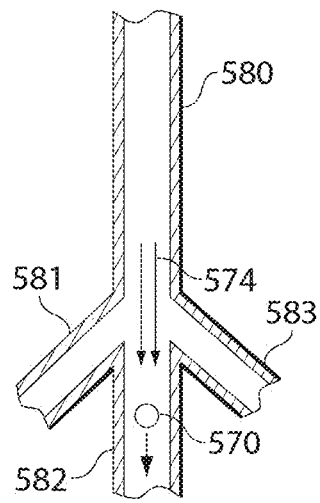
Figure 10D:
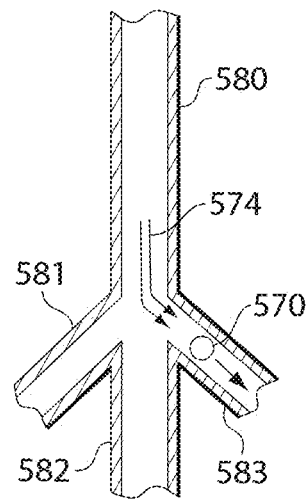

As another example, in FIG. 9A, channel 540, carrying fluidic droplet 530 and liquid 535, divides into channel 542 and 544. Fluidic droplet 530 may be electrically charged, or it may uncharged. Electrode 526 is positioned near channel 542, while electrode 527 is positioned near channel 544. Electrode 528 is positioned near the junction of channels 540, 542, and 544. When fluidic droplet 530 reaches the junction, it may be subjected to an electric field, and/or directed to a channel or other region, for example, by directing the surrounding liquid into the channel. As shown in FIG. 9B, fluidic droplet 530 may be split into two separate droplets 565 and 566 by applying an electric field 525 to the droplet using electrodes 526 and 527. In FIG. 9C, a dipole can be induced in droplet 530 by applying an electric field 525 to the droplet using electrodes 527 and 528. Due to the strength of the applied electric field, the droplet may be strongly attracted to the right, into channel 544. Similarly, in FIG. 9D, a dipole may be induced in droplet 530 by applying an electric field 525 to the droplet using electrodes 526 and 528, causing the droplet to be attracted into channel 542. By controlling which electrodes are used to induce an electric field across droplet 530, and/or the strength of the applied electric field, one or more fluidic droplets within channel 540 may be sorted and/or split into two droplets, and each droplet may independently be sorted and/or split.

Sensing Droplets; Sensing the Content of Droplets

In certain aspects of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

In some cases, the sensor may be connected to a processor, which in turn, cause an operation to be performed on the fluidic droplet, for example, by sorting the droplet, adding or removing electric charge from the droplet, fusing the droplet with another droplet, splitting the droplet, causing mixing to occur within the droplet, etc., for example, as previously described. For instance, in response to a sensor measurement of a fluidic droplet, a processor may cause the fluidic droplet to be split, merged with a second fluidic droplet, etc.

One or more sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc.

As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic.

For example, the sensor may detect capacitance, inductance, etc., of a fluidic droplet and/or the portion of the fluidic system containing the fluidic droplet.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

As a particular non-limiting example, a device of the invention may contain fluidic droplets containing one or more cells. The cells may be exposed to a fluorescent signal marker that binds if a certain condition is present, for example, the marker may bind to a first cell type but not a second cell type, the marker may bind to an expressed protein, the marker may indicate viability of the cell (i.e., if the cell is alive or dead), the marker may be indicative of the state of development or differentiation of the cell, etc., and the cells may be directed through a fluidic system of the invention based on the presence/absence, and/or magnitude of the fluorescent signal marker. For instance, determination of the fluorescent signal marker may cause the cells to be directed to one region of the device (e.g., a collection chamber), while the absence of the fluorescent signal marker may cause the cells to be directed to another region of the device (e.g., a waste chamber). Thus, in this example, a population of cells may be screened and/or sorted on the basis of one or more determinable or targetable characteristics of the cells, for example, to select live cells, cells expressing a certain protein, a certain cell type, etc.

Definitions

A variety of definitions are now provided which will aid in understanding various aspects of the invention. Following, and interspersed with these definitions, is further disclosure that will more fully describe the invention. As noted, various aspects of the present invention relate to droplets of fluid surrounded by a liquid (e.g., suspended). The droplets may be of substantially the same shape and/or size, or of different shapes and/or sizes, depending on the particular application. As used herein, the term "fluid" generally refers to a substance that tends to flow and to conform to the outline of its container, i.e., a liquid, a gas, a viscoelastic fluid, etc. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be essentially immiscible within the time frame of formation of a stream of fluids, or within the time frame of reaction or interaction. Where the portions remain liquid for a significant period of time, then the fluids should be essentially immiscible. Where, after contact and/or formation, the dispersed portions are quickly hardened by polymerization or the like, the fluids need not be as immiscible. Those of ordinary skill in the art can select suitable miscible or immiscible fluids, using contact angle measurements or the like, to carry out the techniques of the invention.

As used herein, a first entity is "surrounded" by a second entity if a closed planar loop can be drawn around the first entity through only the second entity. A first entity is "completely surrounded" if closed loops going through only the second entity can be drawn around the first entity regardless of direction (orientation of the loop). In one embodiment, the first entity is a cell, for example, a cell suspended in media is surrounded by the media. In another embodiment, the first entity is a particle. In yet another embodiment, the first entity is a fluid. The second entity may also be a fluid in some cases (e.g., as in a suspension, an emulsion, etc.), for example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are essentially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, salt solutions, etc., as well as other hydrophilic liquids such as ethanol. Examples of hydrophobic liquids include, but are not limited to, oils such as hydrocarbons, silicone oils, mineral oils, fluorocarbon oils, organic solvents etc. Other examples of suitable fluids have been previously described.

Similarly, a "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

As mentioned, in some, but not all embodiments, the systems and methods described herein may include one or more microfluidic components, for example, one or more microfluidic channels. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria. The "cross-sectional dimension" of the channel is measured perpendicular to the direction of fluid flow within the channel. Thus, some or all of the fluid channels in microfluidic embodiments of the invention may have maximum cross-sectional dimensions less than 2 mm, and in certain cases, less than 1 mm. In one set of embodiments, all fluid channels containing embodiments of the invention are microfluidic or have a largest cross sectional dimension of no more than 2 mm or 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to various components or systems of the invention. In one set of embodiments, the maximum cross-sectional dimension of the channel(s) containing embodiments of the invention is less than 500 microns, less than 200 microns, less than 100 microns, less than 50 microns, or less than 25 microns.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

In one set of embodiments, the fluidic droplets may contain cells or other entities, such as proteins, viruses, macromolecules, particles, etc. As used herein, a "cell" is given its ordinary meaning as used in biology. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

Materials

A variety of materials and methods, according to certain aspects of the invention, can be used to form any of the above-described components of the systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces.

Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials. In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

The following examples are intended to illustrate certain embodiments of the present invention, but do not exemplify the full scope of the invention.

EXAMPLE 1

Figure 15A:
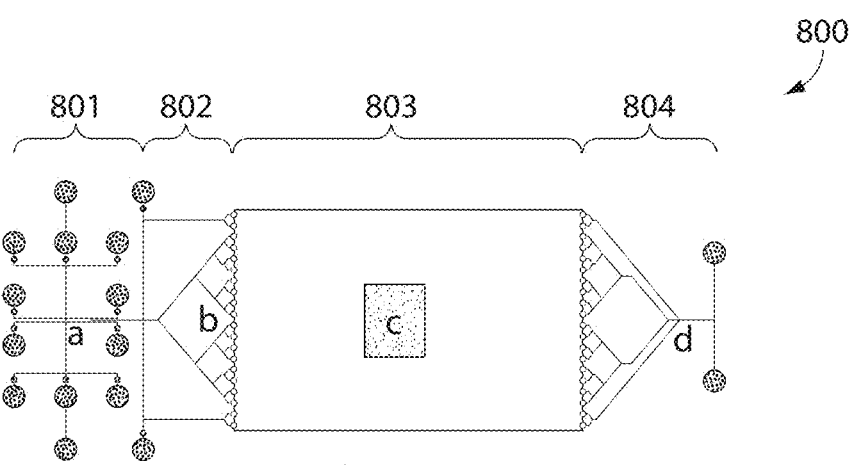
FIGS. 15A-15E illustrate an example of a device featuring various embodiments of the invention.
Figure 15B:
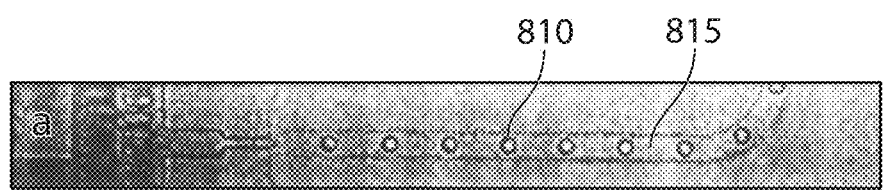

FIG. 15A illustrates an example of a fluidic system having some of the features described above. In this example, fluidic droplets are introduced into fluidic system 800 (shown schematically in FIG. 15A. Fluidic system 800 comprises an inlet region 801 (labeled "a"), a bifurcation region 802 ("b"), a region comprising posts 803 ("c"), and a collection region 804 ("d"). Inlet region 801 produces a series of droplets 810 contained within liquid 815. The droplets have an average diameter of about 20 micrometers. The liquid, in this example, is water, and the fluidic droplets comprise hexadecane with about 3 wt % SPAN80 (a surfactant). The series of droplets are illustrated in FIG. 15B, which is an enlargement of inlet region 801 shown schematically in FIG. 15A.

Figure 15C:
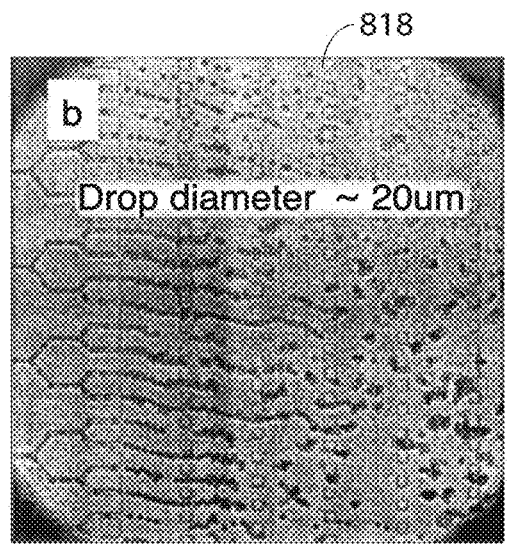
Figure 15D:
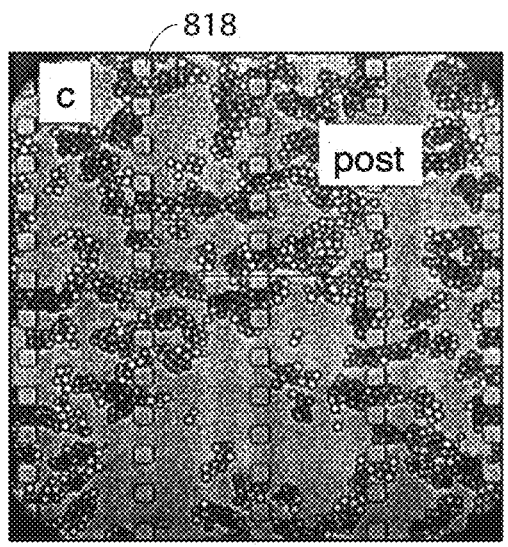
Figure 15E:
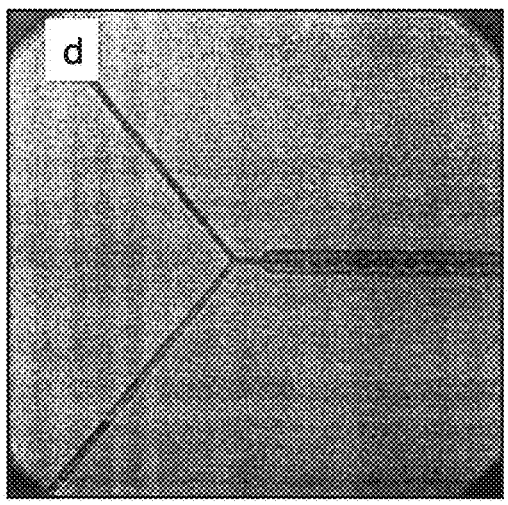

In FIG. 15C, a series of bifurcations (shown to the left of the photomicrograph) divide the fluidic droplets into a series of channels. Since the droplets are not purposefully directed towards any particular channel, the droplets are randomly dispersed within the channels. The droplets are then carried to a region comprising a series of posts 818. An enlargement of this region is illustrated in FIG. 15D. As can be seen, the individual droplets maintain their individual identities and do not fuse, due to the presence of the surfactant. In FIG. 15E, the droplets are collected in collection region 804.

EXAMPLE 2

In this example, precision manipulation of streams of fluids with a microfluidic device is demonstrated. This technology enables high throughput reactors that use minute quantities of reagents. As the scale of these reactors shrinks, contamination effects due to surface adsorption and diffusion may restrict the smallest quantities that can be used. Confinement of reagents in droplets in an immiscible carrier fluid may overcome these limitations, but demands new fluid-handling technology. An example platform technology is presented based on charged droplets and electric fields that enables electrically addressable droplet generation, highly efficient droplet coalescence, precision droplet breaking and recharging, and controllable droplet sorting.

In this example, a generic and robust platform technology is presented for manipulating and controlling individual droplets in a microfluidic device. By combining electrostatic charge on the droplets and electric fields on the devices modules that create, recombine, split, and sort droplets individually are illustrated, providing exquisite control over individual microreactors while retaining high purity and enabling very high throughput. By incorporating the forces that result from charging the aqueous fluid in an electric field, E, smaller droplets are produced with more precise control of their individual timing than is feasible with other strategies that rely solely on viscous forces to overcome surface tension; this provides a robust droplet generation module that allows the production of microreactors with volumes as small as femtoliters. Incorporating charge of opposite signs on different droplets allows droplets to be controllably and reliably merged, overcoming the stabilizing forces due to surface tension and lubrication; this provides a robust droplet coalescence module that allows the precise mixing of aliquots of reactants. By incorporating the extensional force induced by an electric field large droplets may be controllably split into smaller aliquots for further analysis, and in some cases, it may simultaneously recharge neutral droplets for further processing; this provides a robust splitting or charging module that allows multiple assays to be performed on the same materials. By incorporating the forces produced by electric fields on charged droplets, individual droplets may be steered into selected channels; this provides a robust droplet sorting module that allows desired reaction products to be selected. These modules are useful for high speed manipulation and control of individual droplets, and can serve as the technology for droplet-based microfluidic devices.

Moreover, because all control is achieved by switching electric fields, there are no moving parts and frequencies as high as 106 Hz are feasible; this facilitates very high throughput combinatorial technology.

Soft lithography was used to pattern channels in polydimethylsiloxane (PDMS), a transparent polymer material. A glass slide forms the top of the channel. Electric fields were incorporated by patterning indium-tin-oxide (ITO) electrodes on the surface of the glass slide adjacent to the channels and seal the slide to the PDMS using an oxygen plasma. Devices fabricated in PDMS have the advantage of being strongly hydrophobic ensuring that the oil carrier phase wets their surfaces and that the water droplets do not contact the walls of the channel walls, facilitating the isolation of biomolecules and eliminating cross contamination due to surface interactions.

A flow-focusing geometry was used to form the droplets. A water stream was infused from one channel through a narrow constriction; counter propagating oil streams hydrodynamically focus the water stream reducing its size as it passes through the constriction. This droplet generator can be operated in a flow regime that produces a steady stream of uniform droplets of water in oil. The size of the water droplets was controlled by the relative flow rates of the oil and the water; the viscous forces overcome surface tension to create uniform drops. If the flow rate of the water was too high a longer jet of fluid passes through the orifice and breaks up into droplets further downstream; these droplets were less uniform in size. If the flow rate of the water was too low, the droplet breakup in the orifice becomes irregular, producing a wider range of droplet sizes.

Electric fields were then incorporated to create an electrically addressable emulsification system. To achieve this, high voltage was applied to the aqueous stream and charge the oil water interface. The water stream behaved as a conductor while the oil was an insulator; electrochemical reactions charged the fluid interface like a capacitor. At snap-off, the charge on the interface remains on the droplet. In addition, the droplet volume, $V_d$, and frequency, f, could be tailored over at least three orders of magnitude without changing the infusion rate of the oil or water. Droplet size and frequency were not independent in this example; instead their product is determined by the infusion rate of the dispersed phase $Q_d=fV_d$. The droplet size decreased with increasing field strength. At low field strength, the droplet size was determined by the flowrate of the continuous phase. However, at high field strength, droplet size was determined by the electric field and decreased rapidly with E.

The dependence of the droplet size on applied voltage for three different flow rates is as follows. At low applied voltages the electric field had a negligible effect, and droplet formation was driven by the competition between surface tension and viscous flow. By contrast, at high electric field strengths, there was a significant additional force on the growing drop, F=qE, where q is the charge on the droplet. Since the droplet interface behaved as a capacitor, q is proportional to the applied voltage, V. This led to a V 2 dependence of the force, which accounted for the decrease in droplet size with increasing applied field. For even higher electric fields, the charged interface of the water stream was repelled by the charged drops.

In one embodiment, oil and water streams converge at 30 micron orifice. A voltage V applied to indium-tin-oxide (ITO) electrodes on the glass produced an electric field E to capacitively charge the aqueous-oil interface. Droplet size was found to be independent of charge at low field strengths but decreased at higher fields. Droplet size is a function of voltage, showing the crossover between flow-dominated and field-dominated snap-off for three different flow rates of the continuous phase oil ($Qc=80$ nL/s, 110 nL/s, and 140 nL/s). The infusion rate of the water was constant at $Qd=20$ nL/s.

The electronic control afforded by the field-induced droplet formation provides an additional benefit in this example: it allowed the phase of the droplet break-off to be adjusted within the production cycle. This was accomplished by increasing the field above the critical break-off field only at the instant the droplet is required. This provided a convenient means to precisely synchronize the production and arrival of individual droplets in specific locations.

An important component in some droplet-based reaction confinement system is a mixer which combines two or more reagents to initiate a chemical reaction. An example of a mixer uses electrostatic charges; placing charges of opposite sign on each droplet and applying an electric field causes them to coalesce. As an example, a device is illustrated having two separate nozzles that generate droplets with different compositions and opposite charges. Droplets were brought together at the confluence of the two streams. The electrodes used to charge the droplets upon formation also provide the electric field to force the droplets across the stream lines, leading to coalesce. Slight variations in the structure of the two nozzles resulted in slight differences in the frequency and phase of their droplet generation in the absence of a field. Thus the droplets differed in size, even though the infusion rates were identical. Moreover, the droplets did not arrive at the point of confluence at exactly the same time. As a result the droplets did not coalesce. By contrast, upon application of an electric field, droplet formation became generally synchronized, ensuring that pairs of identically sized droplets reached the point of confluence simultaneously. Moreover, the droplets were oppositely charged, causing them to traverse the stream lines and contact each other thereby causing them to coalesce. The synchronization of droplet formation resulted from coupling of the break-off of the two droplets as mediated by the electric field; the magnitude of the electric field varied as the separation between the leading edges of the two droplets changes and the frequency of droplet break-off is mode locked to the electric field. A minimum charge is required to cause droplets to coalesce in this example, presumably because of the stabilizing effects of the surfactant coating; the E field depends on the percentage of droplets that contacted each other that actually coalesce.

In one embodiment, droplets having opposite sign of electrostatic charge can be generated by applying a voltage across the two aqueous streams. In another embodiment, in the absence of the field, the frequency and timing of droplet formation at the two nozzles may be independent, and each nozzle may produce a different size droplet at a different frequency; infusion rates are the same at both nozzles. After the confluence of the two streams, droplets from the upper and lower nozzles stay in their respective halves of the stream. Due to surfactant, there are no coalescence events even in the case of large slugs that fill the channel width. In yet another embodiment, with an applied voltage of 200V across the 500 micron separation of the nozzles, the droplets that simultaneously break-off from the two nozzles are essentially identical;

simultaneous droplet formation can be achieved for unequal infusion rates of the aqueous streams even up to a factor of two difference in volumes. The fraction of the droplets that encounter each other and coalesce increases linearly above a critical field when a surfactant, sorbiton-monooleate 3% is present.

The use of oppositely charged droplets and an electric field to combine and mix reagents was extremely robust, and nearly 100% of the droplets from the two streams coalesced with their partners from the opposite stream. However, after they coalesced the resultant droplets carried essentially no electrostatic charge. While it is convenient to charge droplets during formation, other methods may be employed in any robust droplet-based microfluidic system to recharge the mixed droplets, if necessary, for further processing. This may be accomplished, for example, through the use of extensional flow to split neutral droplets in the presence of an electric field which polarizes the droplets resulting in two oppositely charged daughter droplets. In one embodiment, neutral droplets enter a bifurcation and split into charged daughter droplets. In some cases, the asymmetric stretching of the charged droplets in the electric field can be observed. The vertical dashed lines indicate the edge of the electrodes where the droplets returned to their symmetric spherical shape. The electric field also allowed precision control of the droplet splitting, providing the basis of a robust droplet division module which allows the splitting of the contents into two or more aliquots of identical reagent facilitating multiple assays on the contents of the same microreactor.

In another embodiment, neutral droplets can be recharged by breaking them in the presence of an electric field. Uncharged droplets ($q=0$) were polarized in an electric field (ES not equal to 0), provided ES was sufficiently large, and the droplets break into two oppositely charged daughter drops in the extensional flow at a bifurcation. The charged droplets were stretched in the electric field ES, but returned to spherical on contacting the electrodes.

Another component useful for the construction of microfluidic droplet reaction systems is a droplet sorter. The contents of individual may must be probed, and selected droplets may be sorted into discreet streams. Such sorting in microfluidic devices can be accomplished, as shown in this example, through the use of mechanical valves. The use of electrostatic charging of droplets may provide an alternate means that can be precisely controlled, can be switched at high frequencies, and requires no moving parts. Electrostatic charge on the droplets may enable drop-by-drop sorting based on the linear coupling of charge to an external electric field. A T-junction bifurcation that splits the flow of carrier fluid equally will also randomly split the droplet population equally into the two streams. However, a small electric field applied at the bifurcation may precisely dictate which channel the droplets enter; varying the direction of the field varies the direction of the droplet sorting. The large forces that can be imparted on the droplets and the high switching frequency make this a fast and robust sorting engine with no moving parts; thus the processing rate is limited primarily by the rate of droplet generation.

In one embodiment, charged droplets alternately entered the right and left channels when there was no field applied (ES=0). When an electric field is applied to the right, the droplets entered the right branch at the bifurcation; they entered the left branch when the field is reversed. After the bifurcation, the distance between droplets is reduced to half what it was before, indicating the oil stream is evenly divided. In some cases, the deformation in the shape of a highly charged drop in an electric field can be observed.

The enhanced functionality that electrostatic charge brings to droplets in microfluidic devices enables an expansive list of microfluidics applications. This toolkit of techniques for manipulating droplets will enable modular integration of systems for transporting and reacting small numbers of molecules. High throughput screening, combinatorial chemistry, and the search for rare biological function in libraries could all potentially benefit from electrostatic manipulation of droplets in microchannels. For instance, droplet based microfluidic technology can also be used to develop a chip-scale fluorescence activated cell sorter (FACS) with enhanced activation functionality that goes beyond fluorescence to include multiple reagent-based assays between the droplet formation and sorting steps. Moreover by using femtoliter drops, which are a few microns in diameter, even a single biomolecule represents a concentrations of >>1 nM, sufficient for efficient chemical reactivity and single molecule assays.

Many of the uses of droplet-based microfluidic devices are driven by a need to encapsulate a varied population or library of molecules, cells or particles into microreactors, perform an assay on the contents, perhaps through the addition of reagents, and then, finally, to selectively remove specific microreactors from the collection in a search for rare events. This requires a processing rate of 103 per second to sort through the smallest libraries in a reasonable time while rates on the order 105 per second are desirable for larger libraries. These rates are feasible, as discussed herein. Moreover, because the microfluidic devices may be produced using stamping techniques, e.g., as described herein, parallel flow streams or fluidic systems can be fabricated, further enhancing the total throughput. Combined, the advantages of droplets and high throughput manipulation provide significant opportunity for widespread application.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of introducing a fluid into a droplet, comprising:
    flowing a plurality of liquid droplets through a first microchannel in a carrier liquid, wherein each of the plurality of liquid droplets comprises a first liquid that is immiscible with the carrier liquid;
    flowing a single phase liquid stream in a second microchannel, wherein the second microchannel intersects the first microchannel at an opening into the first microchannel;
    directly injecting a portion of the single phase liquid stream that is flowing in the second microchannel into each of the plurality of liquid droplets as each of the plurality of liquid droplets in the first microchannel comes into contact with the opening of the second microchannel, thereby introducing a portion of the single phase liquid stream into each of the plurality of liquid droplets to form mixed liquid droplets; and
    collecting at least a portion of the mixed liquid droplets in a collection region operably associated with the first microchannel and downstream from the intersection of the first and second microchannels, wherein the mixed liquid droplets contact each other but do not fuse with each other.

2. The method of claim 1, wherein the first liquid and the single phase liquid stream comprise hydrophilic liquids.

3. The method of claim 2, wherein the first liquid and the single phase liquid stream comprise aqueous solutions.

4. The method of claim 1, wherein the carrier liquid comprises a hydrophobic liquid.

5. The method of claim 1, wherein the first liquid and the single phase liquid stream comprise a reactant selected from the group consisting of a chemical reagent, a biological entity, and a biochemical entity.

6. The method of claim 5, wherein the first liquid and the single phase liquid stream comprise a reactant selected from the group consisting of a chemical reagent, a biological entity, and a biochemical entity,
    wherein the reactant in the single phase liquid is different than the reactant in the first liquid.

7. The method of claim 1, wherein the first microchannel has a maximum cross-sectional dimension of less than about 500 micrometers.

8. The method of claim 1, further comprising mixing, in at least a portion of the mixed liquid droplets, the portion of the single phase liquid stream with the first liquid.

9. The method of claim 1, further comprising:
    detecting electromagnetic radiation arising from the mixed liquid droplets after the directly injecting step using a sensor.

10. The method of claim 9, further comprising:
    performing an operation on the mixed liquid droplets in response to the detected electromagnetic radiation.

11. The method of claim 1, wherein the directly injecting is carried out under an electric field.

* * * * *